(12) United States Patent
Daubress et al.

(10) Patent No.: US 7,488,354 B2
(45) Date of Patent: Feb. 10, 2009

(54) DYEING COMPOSITION COMPRISING AT LEAST ONE DISULPHIDE DYE AND METHOD OF DYEING HUMAN KERATIN FIBERS USING THIS DYE

(75) Inventors: Nicolas Daubress, la Celles St cloud (FR); Gilles Genain, Paris (FR)

(73) Assignee: L'Oreal S.A., Paris (FR)

( * ) Notice: Subject to any disclaimer, the term of this patent is extended or adjusted under 35 U.S.C. 154(b) by 497 days.

(21) Appl. No.: 11/249,357

(22) Filed: Oct. 14, 2005

(65) Prior Publication Data

US 2006/0080791 A1 Apr. 20, 2006

Related U.S. Application Data

(60) Provisional application No. 60/629,308, filed on Nov. 19, 2004.

(30) Foreign Application Priority Data

Oct. 14, 2004 (FR) .................. 04 10864

(51) Int. Cl.
*A61Q 5/10* (2006.01)
*C09B 31/02* (2006.01)

(52) U.S. Cl. .............. 8/405; 8/406; 8/409; 8/410; 8/412; 8/426; 8/432; 8/435; 8/437; 8/565; 8/567; 8/568; 8/570; 132/202; 132/208; 534/759

(58) Field of Classification Search .............. 8/405, 8/406, 410, 412, 432, 435, 565, 566, 567, 8/568, 570, 426, 437; 132/202, 208; 534/759
See application file for complete search history.

(56) References Cited

U.S. PATENT DOCUMENTS

| | | | |
|---|---|---|---|
| 2,904,385 | A | 9/1959 | Charle et al. |
| 3,100,739 | A | 8/1963 | Kaiser et al. |
| 3,524,842 | A | 8/1970 | Grossmann et al. |
| 3,578,386 | A | 5/1971 | Kalopissis et al. |
| 3,617,163 | A | 11/1971 | Kalopissis et al. |
| 3,817,698 | A | 6/1974 | Kalopissis et al. |
| 3,867,456 | A | 2/1975 | Kalopissis et al. |
| 3,955,918 | A | 5/1976 | Lang |
| 4,025,301 | A | 5/1977 | Lang |
| 4,151,162 | A | 4/1979 | Lang et al. |
| 4,153,065 | A | 5/1979 | Lang |
| 4,226,784 | A | 10/1980 | Kalopissis et al. |
| 4,823,985 | A | 4/1989 | Grollier et al. |
| 4,886,517 | A | 12/1989 | Bugaut et al. |
| 5,708,151 | A | 1/1998 | Möckli |
| 5,879,413 | A | 3/1999 | Pengilly et al. |
| 5,888,252 | A | 3/1999 | Möckli |
| 5,919,273 | A | 7/1999 | Rondeau et al. |
| 5,993,490 | A | 11/1999 | Rondeau et al. |
| 6,045,591 | A | 4/2000 | Deneulenaere |
| 6,136,042 | A | 10/2000 | Maubru |
| 6,179,881 | B1 | 1/2001 | Henrion et al. |
| 6,458,167 | B1 | 10/2002 | Genet et al. |
| 6,492,502 | B2 | 12/2002 | Henrion et al. |
| 6,797,013 | B1 | 9/2004 | Lang et al. |
| 6,863,883 | B1 | 3/2005 | Tsujino et al. |
| 7,056,346 | B1 | 6/2006 | Maubru |
| 2001/0001332 | A1 | 5/2001 | Henrion et al. |
| 2002/0165368 | A1 | 11/2002 | Henrion et al. |
| 2004/0187225 | A1 | 9/2004 | Vidal et al. |
| 2004/0237213 | A1 | 12/2004 | Plos et al. |

FOREIGN PATENT DOCUMENTS

| | | |
|---|---|---|
| DE | 25 27 638 A1 | 5/1976 |
| DE | 25 38 363 A1 | 5/1976 |
| DE | 41 37 005 A1 | 5/1993 |
| DE | 42 20 388 A1 | 12/1993 |
| EP | 0 271 322 A2 | 6/1988 |
| EP | 0 318 294 A2 | 5/1989 |
| EP | 0 714 954 A2 | 6/1996 |
| EP | 0 850 636 A1 | 7/1998 |
| EP | 0 850 637 A1 | 7/1998 |
| EP | 0 918 053 A1 | 5/1999 |
| EP | 0 920 856 A1 | 6/1999 |
| EP | 1 062 940 A1 | 12/2000 |
| EP | 1 133 975 A2 | 9/2001 |
| EP | 1 333 976 A2 | 9/2001 |
| FR | 1 156 407 | 5/1958 |
| FR | 1 221 122 | 5/1960 |
| FR | 1 516 943 | 5/1968 |
| FR | 1 540 423 | 9/1968 |
| FR | 1 560 664 | 3/1969 |
| FR | 1 567 219 | 5/1969 |
| FR | 2 189 006 | 1/1974 |
| FR | 2 275 462 | 1/1976 |
| FR | 2 285 851 | 4/1976 |
| FR | 2 570 946 A1 | 4/1986 |
| FR | 2 586 913 A1 | 3/1987 |
| FR | 2 757 385 A1 | 6/1998 |
| FR | 2 788 433 A1 | 7/2000 |

(Continued)

OTHER PUBLICATIONS

STIC Search Report dated Apr. 23, 2008.*

(Continued)

*Primary Examiner*—Eisa B Elhilo
(74) *Attorney, Agent, or Firm*—Finnegan, Henderson, Farabow, Garrett & Dunner LLP

(57) ABSTRACT

Disclosed herein is a dyeing composition comprising a particular disulphide dye and a method of dyeing human keratin fibers, such as hair, using this composition. This composition makes it possible to obtain particularly fast chromatic colorations.

57 Claims, No Drawings

FOREIGN PATENT DOCUMENTS

| | | |
|---|---|---|
| FR | 2 822 696 A1 | 10/2002 |
| FR | 2 825 624 A1 | 12/2002 |
| GB | 738 585 | 10/1955 |
| GB | 1 163 385 | 9/1969 |
| GB | 1 195 386 | 6/1970 |
| GB | 1 514 466 | 6/1978 |
| WO | WO 95/01772 | 1/1995 |
| WO | WO 95/15144 | 6/1995 |
| WO | WO 97/44004 | 11/1997 |
| WO | WO 99/48465 | 9/1999 |
| WO | WO 01/66646 A1 | 9/2001 |
| WO | WO 03/029359 A1 | 4/2003 |
| WO | WO 03/099242 A1 * | 12/2003 |

OTHER PUBLICATIONS

Guido Alberti et al., "Cationic Dyes for Acrylic Fibres, V. Cationic Dyes Derived from Several Heteroyclic Amines With Two or More Heteroatoms," Annali di Chimica, vol. 65, pp. 305-314 (1975).

G. Alberti et al., "Richerce Sui Coloranti Cationici Per Fibra Acrilica," La Chimica E L'Industria, vol. 56, No. 9, pp. 600-603 (1974).

Guido Alberti et al., "Thermodynamic Features in Acrylic Fiber Dyeing with Basic Dyes," Textile Research Journal, pp. 105-107 (1984).

Alexandru T. Balaban et al., "Reactions of Pyryliuim Salts with Nucleophiles, XX. Synthesis of 4-(N-pyridinium)-4'-dialkylaminoazobenzene and of 4-(4-dialkylaminophenylazo)-4'-(N-pyridinium)-Biphenyl Derivaties," Revue Roumaine de Chemie, vol. 3, No. 4, pp. 377-383 (1988).

Zh. Obshch. Khim., vol. 40, No. 1, pp. 195-202, (1970).

A.F. Kuznetsova et al., "The Determination of Thickness of a Histological Section by Interference Microscopy," Tsitologiya, vol. 10, No. 3, pp. 403-405, (1968).

D.M. Lewis et al., "The role of vinylsulphonyl reactive dyes in prevention of wool damage," JSDC, vol. 107, pp. 357-362 (1991).

Richard Neidlein et al., "Synthese von substituierten Pyridiniumsalzen," Monatshefte für Chemie, vol. 106, pp. 643-648 (1975).

Piero Savarino et al., "Disperse and Cationic Dyes from Aminophenyl-X-Azolo-Pyridines," Dyes and Pigments, vol. 11, pp. 163-172 (1989).

Von Eberhard Seidler et al., "Die Eignung verschiedener Ditetrazoliumsalze als Reduktionsindikatoren in der Enzymhistochemie," Acta Histochem., vol. 61, No. 1, pp. 48-52, (1978).

Guido Viscardi et al., "Disperse and Cationic Azo Dyes from heterocyclic Intermediates," Dyes and Pigments, vol. 19, pp. 69-79 (1992).

Feng-Wen Yen et al., "The Design and Synthesis of Bisazo Series Compound Used in Organophotoconductor," MRL Bulletin of Research and Development, vol. 6, No. 2, pp. 21-27 (1992).

French Search Report for FR 0410864, dated Jul. 11, 2005, Examiner G. Kyriakakou.

* cited by examiner

DYEING COMPOSITION COMPRISING AT LEAST ONE DISULPHIDE DYE AND METHOD OF DYEING HUMAN KERATIN FIBERS USING THIS DYE

This application claims benefit of U.S. Provisional Application No. 60/629,308 filed Nov. 19, 2004, the contents of which are incorporated herein by reference. This application also claims benefit of priority under 35 U.S.C. § 119 to French Patent Application No. 04 10864, filed Oct. 14, 2004, the contents of which are also incorporated by reference.

The present disclosure relates to a dyeing composition comprising a particular disulphide dye and a method of dyeing keratin fibers, such as human keratin fibers, for example, hair, using this composition. Also disclosed herein is a novel disulphide dye.

It is known to dye keratin fibers, such as human keratin fibers, with a direct dye. The method conventionally used in direct dyeing comprises applying to the keratin fibers direct dyes which are colored and coloring molecules having affinity for the fibers, in allowing them to diffuse, and then in rinsing the fibers.

Direct dyes which are conventionally used are, for example, nitrobenzene dyes, anthraquinone dyes, nitropyridines, and dyes of the azo, xanthene, acridine, azine and triarylmethane types.

Colorations which result from the use of direct dyes are temporary or semi-permanent colorations because the nature of the interactions which bind the direct dyes to the keratin fiber, and their desorption from the surface and/or from the core of the fiber are generally considered responsible for their weak dyeing power and their poor fastness to washing and to perspiration.

It is also known to obtain permanent colorations with dyeing compositions containing oxidation dye precursors, generally called oxidation bases, such as ortho- or para-phenylenediamines, ortho- or para-aminophenols and heterocyclic compounds. These oxidation bases are colorless or faintly colored compounds which, combined with oxidizing products, can give rise, through an oxidative condensation process, to colored compounds.

It is also known that it is possible to vary the shades obtained by combining these oxidation bases with couplers or color modifiers, the latter being chosen, for example, from aromatic meta-diamines, meta-aminophenols, meta-diphenols and certain heterocyclic compounds such as indole compounds.

The variety of molecules used in oxidation bases and couplers makes it possible to obtain a rich palette of colors.

Oxidation dyeing comprises applying to the keratin fibers bases or a mixture of bases and couplers with hydrogen peroxide as oxidizing agent, in allowing to diffuse, and then in rinsing the fibers. The colorations resulting therefrom are permanent, intense and resistant to external agents, such as to light, to adverse weather conditions, to washing, to perspiration and/or to friction.

Oxidation dyeing systems make it possible to obtain background colorations which are relatively shampoo-fast but often they do not make it possible to obtain chromatic shades.

To increase the fastness of direct dyes, it is known to fix the direct dyes via covalent bonding to the hair. For example, it is known to cause dyes with reactive groups to react with the cystine or cysteine residues which are present in very large numbers in the hair fibers. Also described are some dyes bearing Bunte salt and isothiuronium functional groups, or other thiol-protecting groups. However, the production of the reactive form of the dye generally requires the use of strongly basic media. Furthermore, the thiol functional groups are generally generated in excess, which makes a post-neutralizing step following the dyeing necessary.

Other disulphide dyes known for dyeing keratin fibers are disulphide derivatives of aminothiophenol derivatives. Such dyes are described, for example, in French Patent FR 1 156 407. These dyes may be used under relatively mild conditions, in the presence of a slightly reducing medium or after a reducing pretreatment of the hair. However, these dyes can cause color variations during application.

Further, it is known in the article "The role of the vinylsulphonyl reactive dyes in prevention of wool damage", J. Soc. Dyers Colorists, vol. 107, October 1991, p. 357-362 to dye wool at a high temperature (100° C.) with a disulphide dye, the disulphide group serving to generate a vinylsulphonyl group, so as to reduce degradation of the wool fibers.

Thus it would be desirable to provide novel systems for dyeing keratin fibers, for example human keratin fibers, such as hair, which do not have the disadvantages of existing direct dyes. For example, it would be desirable to provide direct dyeing systems which make it possible to obtain chromatic colorations which are very fast, such as being resistant to successive shampooings.

In this regard, the present disclosure relates to a method for dyeing human keratin fibers comprising applying to the fibers a dyeing composition comprising, in an appropriate cosmetic medium, at least one disulphide dye chosen from the dyes of the following formulae (I), (II), (III) or (IV):

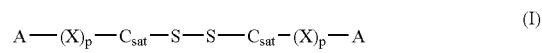

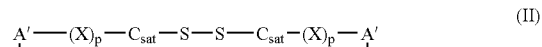

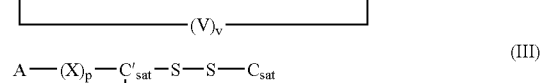

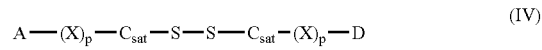

their salts, isomers and solvates such as hydrates, in which formulae:

A and A', which are identical or different, are chosen from radicals comprising at least one cationic or noncationic chromophore;

V and V', which are identical or different, are chosen from bridging groups;

v and v', which are identical or different, are 0 or 1;

X, which are identical or different, are chosen from saturated or unsaturated, linear or branched $C_1$-$C_{30}$ hydrocarbon chains optionally interrupted and/or optionally terminated at one or both ends by at least one divalent group chosen from:

—N(R)—, —N⁺(R)(R)—, —O—, —S—, —CO—, —SO₂— with R, which are identical or different, being chosen from hydrogen and from $C_1$-$C_4$ alkyl, hydroxyalkyl, and aminoalkyl radicals;

an optionally substituted, saturated or unsaturated, fused or nonfused, aromatic or nonaromatic (hetero)cyclic radical optionally comprising at least one identical or different heteroatom;

the coefficient p is equal to 0 or 1;

$C_{sat}$ and $C'_{sat}$, which are identical or different, are chosen from optionally substituted, optionally cyclic, linear or branched $C_1$-$C_{18}$ alkylene chains;

D is a radical chosen from hydroxyl, hydroxyalkyl, alkoxy, carboxyl, carboxylate, amino, alkylamino and dialkylamino radicals.

The method of the present disclosure makes it possible to obtain chromatic colors or background colors which are very fast to shampoos, to common attacks (sun, perspiration) and/or to other hair treatments.

Also disclosed herein is a dyeing composition comprising, in an appropriate cosmetic medium for dyeing keratin fibers, e.g., human keratin fibers, at least one disulphide dye chosen from the dyes of formulae (I), (II), (III) or (IV).

Another embodiment disclosed herein is the use of at least one disulphide dye of formula (I), (II), (III) or (IV) for dyeing keratin fibers, e.g., human keratin fibers, such as hair.

The present disclosure also relates to the disulphide dyes of formulae (I), (II), (III) or (IV), as they are, their salts, their isomers and their solvates.

For the purposes of the present disclosure, and unless otherwise stated:

the aryl or heteroaryl radicals or the aryl or heteroaryl part of a radical may be substituted with at least one substituent carried by a carbon atom, chosen from:

a $C_1$-$C_{16}$, such as $C_1$-$C_8$, alkyl radical optionally substituted with at least one radical chosen from the radicals hydroxyl, $C_1$-$C_2$ alkoxy, $C_2$-$C_4$ (poly)hydroxyalkoxy, acylamino, amino substituted with two $C_1$-$C_4$ alkyl radicals, which are identical or different, optionally bearing at least one hydroxyl group, or it being possible for the two radicals to form, with the nitrogen atom to which they are attached, an optionally substituted, saturated or unsaturated heterocycle comprising from 5 to 7 members, such as 5 or 6 members, optionally comprising another heteroatom which is identical to or different from nitrogen;

a halogen atom such as chlorine, fluorine or bromine;

a hydroxyl group;

a $C_1$-$C_2$ alkoxy radical a $C_2$-$C_4$ (poly)hydroxyalkoxy radical;

an amino radical;

an amino radical substituted with one or two $C_1$-$C_4$ alkyl radicals, which are identical or different, optionally bearing at least one group chosen from hydroxyl and amino groups, or with two optionally substituted $C_1$-$C_3$ alkyl radicals, it being possible for the alkyl radicals to form, with the nitrogen atom to which they are attached, an optionally substituted, saturated or unsaturated heterocycle comprising from 5 to 7 members, optionally comprising at least one other heteroatom different from or identical to nitrogen;

an acylamino (—NR—COR') radical in which the radical R is chosen from a hydrogen atom and a $C_1$-$C_4$ alkyl radical optionally bearing at least one hydroxyl group and the radical R' is a $C_1$-$C_2$ alkyl radical;

a carbamoyl ((R)$_2$N—CO—) radical in which the radicals R, which are identical or different, are chosen from a hydrogen atom and a $C_1$-$C_4$ alkyl radical optionally bearing at least one hydroxyl group;

an alkylsulphonyl amino (R'SO$_2$—NR—) radical in which the radical R is chosen from a hydrogen atom and a $C_1$-$C_4$ alkyl radical optionally bearing at least one hydroxyl group and the radical R' is chosen from a $C_1$-$C_4$ alkyl radical and a phenyl radical;

an aminosulphonyl ((R)$_2$N—SO$_2$—) radical in which the radicals R, which are identical or different, are chosen from a hydrogen atom and a $C_1$-$C_4$ alkyl radical optionally bearing at least one hydroxyl group, a carboxyl radical in acid form or salified form (such as with an alkali metal or an ammonium, substituted or unsubstituted);

a nitro radical;

a nitrile (CN) group;

a trifluoromethyl (CF$_3$) group;

the cyclic or heterocyclic part of a nonaromatic radical may be substituted with at least one substituent carried by a carbon atom chosen from the groups:

hydroxyl, $C_1$-$C_4$ alkoxy, $C_2$-$C_4$ (poly)hydroxyalkoxy, alkylcarbonylamino (RCO—NR'—) in which the radical R' is chosen from a hydrogen atom and a $C_1$-$C_4$ alkyl radical optionally bearing at least one hydroxyl group and the radical R is a $C_1$-$C_2$ alkyl radical, an amino radical substituted with two $C_1$-$C_4$ alkyl groups which are identical or different, optionally bearing at least one hydroxyl group, it being possible for the alkyl radicals to form, with the nitrogen atom to which they are attached, an optionally substituted, saturated or unsaturated heterocycle comprising from 5 to 7 members, optionally comprising at least one other heteroatom different from or identical to nitrogen;

a hydrocarbon chain is unsaturated when it contains one or more double bonds and/or one or more triple bonds;

a heteroaromatic or heteroaryl radical is an aromatic radical in which at least one of the carbon atoms is replaced by a heteroatom chosen from nitrogen, oxygen and sulphur.

Furthermore, unless otherwise stated, the limits delimiting the size of a range of values (endpoints) are included in this range of values.

As used herein, the expression "chromophore" means a radical derived from a dye, i.e., a radical derived from a molecule which absorbs in the visible region of radiation (from 400 to 800 nm).

The radicals A and A' of formulae (I), (II), (III) and (IV) may comprise at least one chromophore, wherein the chromophores are identical or different.

For the purposes of the present disclosure, the chromophores are said to be different when they differ in their chemical structure. Such chromophores may be chromophores derived from different families or from the same family, on condition that they have different chemical structures. For example, the chromophores may be chosen from the family of azo dyes, but differ in the chemical structure of the radicals of which they are composed or in the respective position of these radicals.

As chromophores that are useful herein, mention may be made of radicals derived from the following dyes: acridines, acridones, anthranthrones, anthrapyrimidines, anthraquinones, azines, azos, azomethines, benzanthrones, benzimidazoles, benzimidazolones, benzindoles, benzoxazoles, benzopyrans, benzothiazoles, benzoquinones, bisazines, bisisoindolines, carboxanilides, coumarins, cyanins (such as azacarbocyanins, diazacarbocyanins, diazahemicyanins, hemicyanins and tetraazacarbocyanins), diazines, diketopyrrolopyrroles, dioxazines, diphenylamines, diphenylmethanes, dithiazines, flavonoids such as flavanthrones and flavones, fluorindines, formazans, hydrazones, such as arylhydrazones, hydroxy ketones, indamines, indanthrones, indigoids and pseudo-indigoids, indophenols, indoanilines, isoindolines, isoindolinones, isoviolanthrones, lactones, methines, naphthalimides, naphthanilides, naphtholactams, naphthoquinones, nitro dyes, such as nitro(hetero)aromatic dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, xanthenes.

Among the nitro chromophores that may be used herein, mention may be made in a non-limiting manner of the radicals derived from the following dyes:

1,4-diamino-2-nitrobenzene
1-amino-2-nitro-4-(β-hydroxyethylamino)benzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis-(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-[tris(hydroxymethyl)methylamino]-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene and
1-hydroxy-4-β-hydroxyethylamino-3-nitrobenzene.

Among the azo chromophores that may be used herein, mention may be made of the radicals derived from the cationic azo dyes described in patent applications WO 95/15144, WO 95/01772 and EP-714 954.

Among the azo chromophores that may also be mentioned are those described in the Colour Index International 3rd edition, such as the following compounds:

Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulphonic acid.

Among the quinone chromophores, those mentioned in the abovementioned Colour Index International are suitable, and among these, mention may be made, inter alia, of the radicals derived from the following dyes:

Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:

1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine chromophores, suitable are those listed in the Colour Index International and for example the radicals derived from the following dyes:

Basic Blue 17
Basic Red 2.

Among the triarylmethane chromophores that may be used according to the present disclosure, mention may be made, in addition to those listed in the Color Index, of the radicals derived from the following dyes:

Basic Green 1
Acid Blue 9
Basic Violet 3
Basic Violet 14
Basic Blue 7
Acid Violet 49
Basic Blue 26
Acid Blue 7.

Among the indoamine chromophores that may be used herein, mention may be made of the radicals derived from the following dyes:

2-β-hydroxyethylamino-5-[bis(β-4'-hydroxyethyl)amino]anilino-1,4-benzoquinone;
2-β-hydroxyethylamino-5-(2'-methoxy-4'-amino)anilino-1,4-benzoquinone;
3-N(2'-chloro-4'-hydroxy)phenylacetylamino-6-methoxy-1,4-benzoquinoneimine;
3-N(3'-chloro-4'-methylamino)phenylureido-6-methyl-1,4-benzoquinoneimine;
3-[4'-N-(ethylcarbamylmethyl)amino]phenylureido-6-methyl-1,4-benzoquinoneimine.

Mention may also be made of the chromophores described in documents U.S. Pat. No. 5,888,252, EP 1 133 975, WO 03/029359, EP 860 636, WO 95/01772, WO 95/15144 and EP 714 954. Mention may also be made of those mentioned in the encyclopaedia "The chemistry of synthetic dye" by K. Venkataraman, 1952, Academic Press, vol. 1 to 7, in encyclopaedia "Kirk-Othmer" "Chemical Technology", in the chapter "Dyes and Dye Intermediate", 1993, Wiley & Sons, and in various chapters of the encyclopaedia "Ullmann's Encyclopedia of Industrial Chemistry" 7th edition, Wiley & Sons.

For example, the chromophores are chosen from those derived from dyes of the azo, anthraquinone and/or hydrazone type.

According to one embodiment, A and/or A' of formulae (I), (II), (III) or (IV) comprise at least one cationic radical carried by or included in at least one of the chromophores.

In one embodiment, the cationic radical is a quaternary ammonium.

These cationic radicals are, for example, chosen from alkylammonium, acridinium, benzimidazolium, benzobistriazolium, benzopyrazolium, benzopyridazinium, benzoquinolium, benzothiazolium, benzotriazolium, benzoxazolium, bi-pyridinium, bis-tetrazolium, dihydrothiazolium, imidazopyridinium, imidazolium, indolium, isoquinolinium, naphthimidazolium, naphthoxazolium, naphthopyrazolium, oxadiazolium, oxazolium, oxazolopyridinium, oxonium, phenazinium, phenoxazolium, pyrazinium, pyrazolium, pyrazoyltriazolium, pyridinium, pyridinoimidazolium, pyrrolium, quinolium, tetrazolium, thiadiazolium, thiazolium, thiazolopyridinium, thiazoylimidazolium, thiopyrylium, triazolium and xanthylium radicals.

Examples of cationic chromophores that are useful in the present disclosure have been mentioned above. Other examples are given in patent applications WO 95/01772, WO 95/15144, EP 714 954, EP 318 294 and WO 03/029359.

According to one embodiment, the radicals A, A' in the formulae (I), (II), (III) or (IV) comprise at least one cationic azo chromophore described for example in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 51/15144, GB 1 195 386, U.S. Pat. Nos. 3,524,842, 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

As indicated above, in formulae (I), (II), (III) and (IV), $C_{sat}$ and $C'_{sat}$, independently of each other, are chosen from optionally substituted, optionally cyclic, linear or branched $C_1$-$C_{18}$ alkylene chains. As the substituent, mention may be made of the carboxylate, ester or amide groups, for example, present on the carbon at the beta or gamma position of the sulphur atoms.

In one embodiment, in the case of formulae (I), (II) and (IV), $C_{sat}$ is a —$(CH_2)_n$— chain wherein n is an integer from 1 to 8.

In one embodiment, in the case of formula (III), $C_{sat}$ is a radical —$(CH_2)_n$—, $C'_{sat}$ is a radical —$(CH_2)_n$—C'H—, n having the same meaning as above.

In accordance with one embodiment of the disclosure, in the abovementioned formulae (I), (II), (III) or (IV), when p is equal to 1, X represents the following sequence:

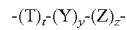

the sequence being linked in formulae (I), (II), (III) or (IV) as follows: —$C_{sat}$(or $C'_{sat}$)-$(T)_t$-$(Y)_y$-$(Z)_z$-(A or A'); in which
T is chosen from at least one radical chosen from —$SO_2$—, —O—, —S—, —N(R)—, —N+(R)(R)—CO—, wherein R is chosen from a hydrogen atom, a $C_1$-$C_4$ alkyl radical and a $C_1$-$C_4$ hydroxyalkyl radical;
the coefficient t is equal to 0 or 1;
Y is chosen from:
  a radical chosen from —$(CH_2)_2$—$SO_2$—;
  —$CH_2$—CHR—CO—NR'— wherein R, R', which are identical or different, are chosen from a hydrogen atom and a $C_1$-$C_4$ alkyl radical.
  a group of formula (a), (a') or (a"):

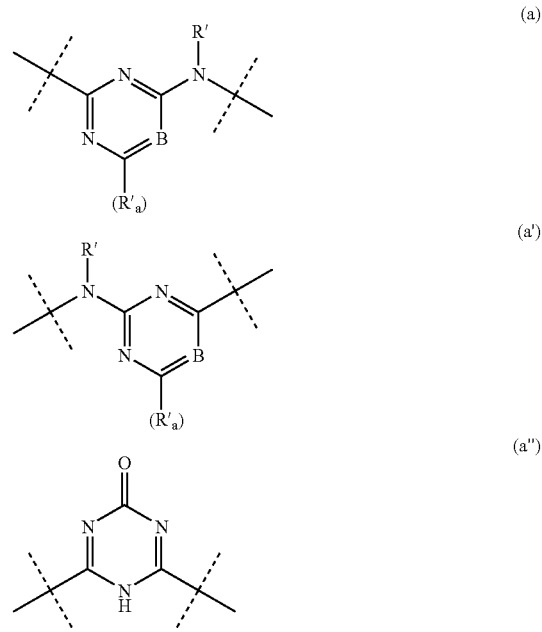

in which
B is chosen from —N—, —$CR_a$, wherein $R_a$ is a hydrogen atom, a halogen atom chosen from chlorine or fluorine, a nitro group, and a pyridinium group which is optionally substituted;
R' has the same definition as above
$R'_a$ is chosen from:
  a hydrogen atom
  a chlorine atom or a fluorine atom
  a pyridinium group which is optionally substituted with at least one group $R_c$, it being possible for $R_c$ to be a $C_1$-$C_4$ alkyl group, a halogen atom, a carboxyl group —COOM (wherein M is a hydrogen atom, an alkali metal, an ammonium group or an ammonium group substituted with at least one linear or branched, identical or different $C_1$-$C_{18}$ alkyl radical, optionally bearing at least one hydroxyl); an ester group —$COOR_d$ with $R_d$ being a $C_1$-$C_4$ alkyl radical; an amide group —$CON(R_d)_2$ with $R_d$, which are identical or different, being chosen from a hydrogen atom and a $C_1$-$C_4$ alkyl radical;

a hydroxyl group an amino, alkylamino or dialkylamino group, wherein the alkyl groups thereof are identical or different $C_1$-$C_{18}$ alkyl groups which are linear or branched, optionally interrupted by a heteroatom chosen from N, O, S, and which are optionally substituted with at least one hydroxyl group, a group NHNHCOR where R is a linear or branched $C_1$-$C_{10}$ alkyl group a group of the following formula (b):

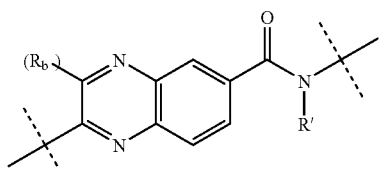

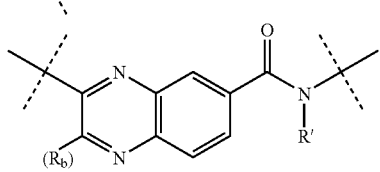

in which

R' has the same definition as above $R_b$ is chosen from a chlorine atom an amino, alkylamino or dialkylamino group, wherein the alkyl groups thereof are identical or different $C_1$-$C_{18}$ alkyl groups which are linear or branched, optionally interrupted by a heteroatom chosen from N, O, S, and which are optionally substituted with at least one hydroxyl group, a saturated or unsaturated nitrogen-containing heterocycle which may be substituted an arylamino group in which the aryl radical may be, for example, $C_6$;

y is equal to 0 or 1;

Z is chosen from

—$(CH_2)_M$— with m being an integer from 1 to 8

—$(CH_2CH_2O)_q$— or —$(OCH_2CH_2)_q$— in which q is an integer from 1 to 15 an aryl, alkylaryl or arylalkyl radical whose alkyl radical is $C_1$-$C_4$ and the aryl radical is, for example, $C_6$, being optionally substituted with at least one group $SO_3M$ wherein M is chosen from a hydrogen atom, an alkali metal, an ammonium group and an ammonium group substituted with at least one identical or different, linear or branched $C_1$-$C_{18}$ alkyl radical optionally bearing at least one hydroxyl group z is equal to 0 or 1.

In at least one embodiment, Y is chosen from one of the groups below,

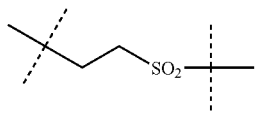

-continued

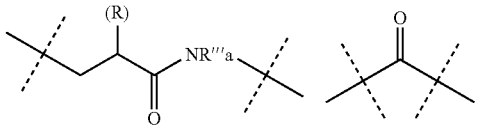

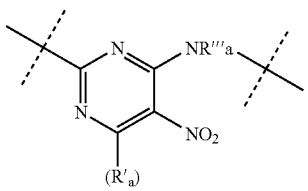

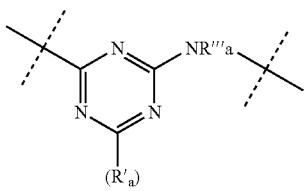

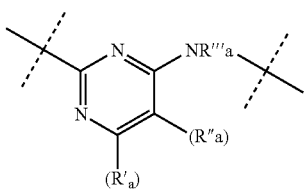

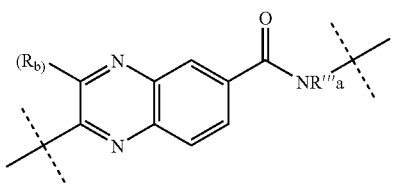

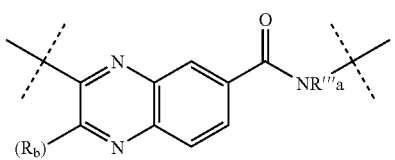

in which the radicals R, $R'_a$ and $R_b$ are as defined above; $R'_a$ has the same definition as $R'_a$, independently of each other; $R'_a$ is chosen from a hydrogen atom and an alkyl radical.

In at least one embodiment, Y is chosen from the following groups:

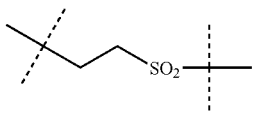

-continued

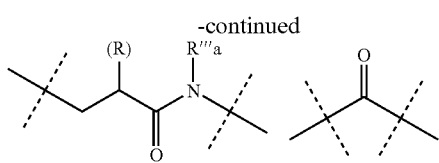

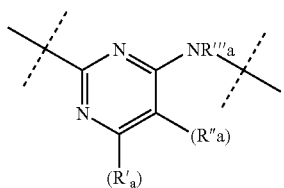

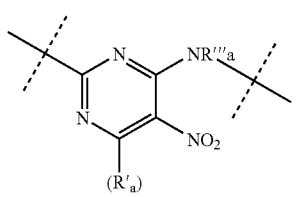

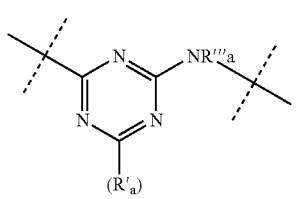

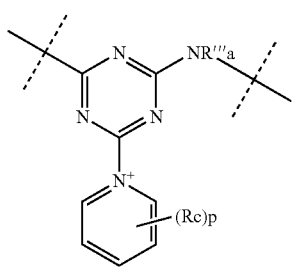

in which

R is chosen from a hydrogen atom and a methyl radical $R'_a$, $R'_a$, which are identical or different, are chosen from chlorine, fluorine and hydrogen atoms $R_c$ is chosen from a $C_1$-$C_4$ alkyl radical; a carboxyl group —COOM wherein M is chosen from a hydrogen atom, an alkali metal, a substituted or unsubstituted ammonium group; an ester group —COOR$_d$ wherein R$_d$ is chosen from a $C_1$-$C_2$ alkyl radical and an amide group —CON(R$_d$)$_2$ wherein R$_d$, which are identical or different, are chosen from a hydrogen atom and a $C_1$-$C_2$ alkyl radical $R'_a$ is chosen from a hydrogen atom and an alkyl radical, for example, a $C_1$-$C_2$ radical, and p ranges from 0 to 2.

Moreover, according to one embodiment of the invention, Z is chosen from:

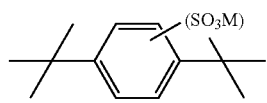

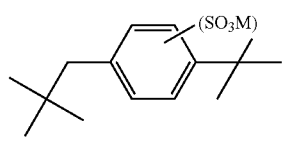

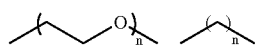

As indicated above, in formula (II), V is a group bridging the two radicals A' which are identical or different and v may be equal to 0 or 1.

In one embodiment, the group V bridging the two chromophores A' is a $C_1$-$C_8$ alkyl radical optionally terminated at one of its two ends by a group chosen from amine, amide or ester.

In accordance with one embodiment of the present disclosure, the disulphide dye is chosen such that v is equal to 0.

By way of examples, the disulphide dye is chosen from:

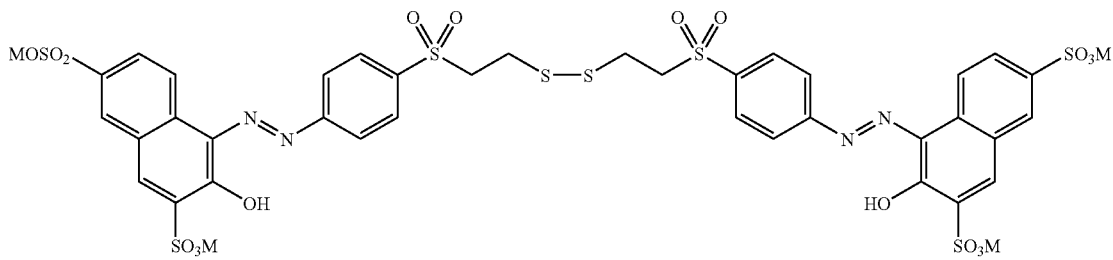

wherein M is chosen from a hydrogen atom, an alkali metal, an ammonium group and an ammonium group substituted with at least one identical or different, linear or branched $C_1$-$C_{10}$ alkyl radical optionally bearing at least one hydroxyl group, and the following compounds, in acidic, basic or neutralized form:
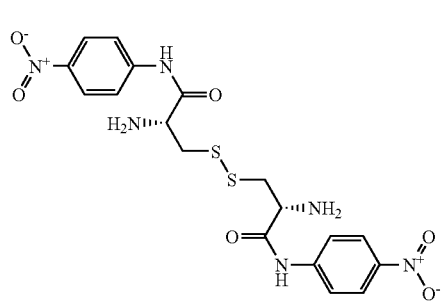
(1)
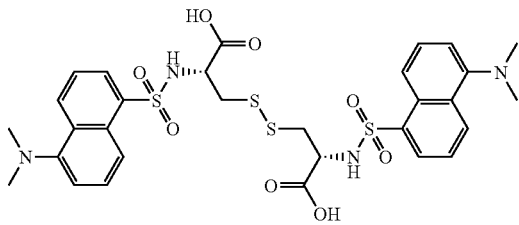
(2)
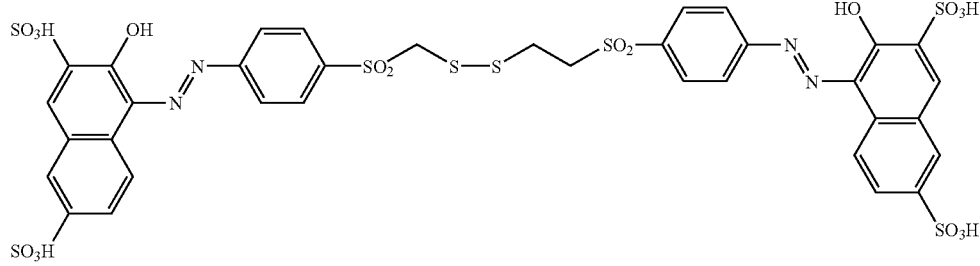
(3)
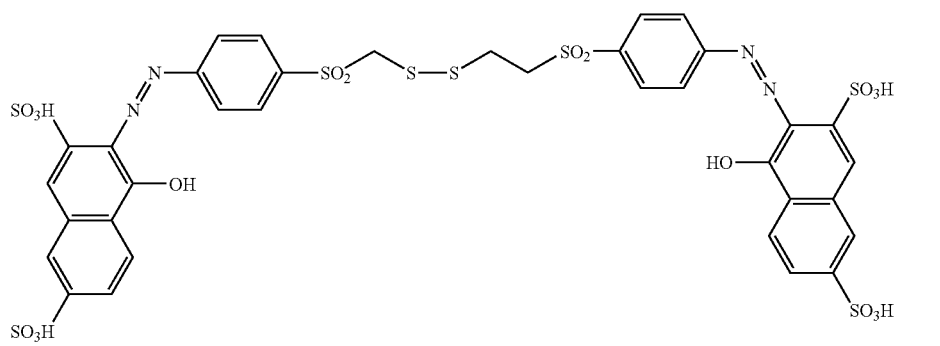
(4)
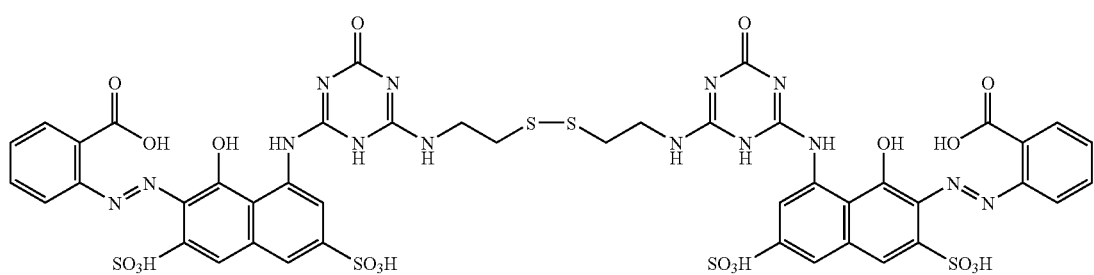
(5)
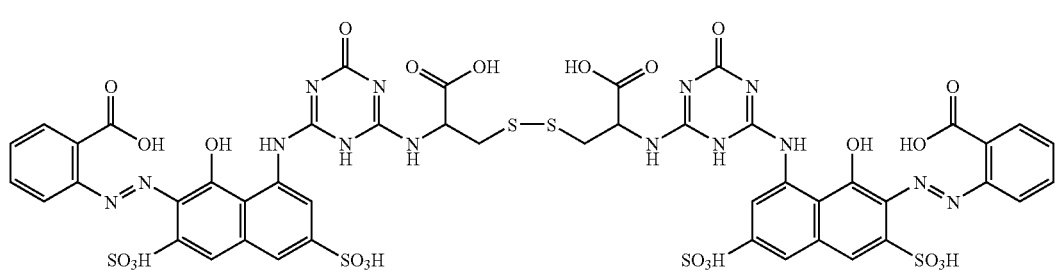
(6)

-continued
(7)
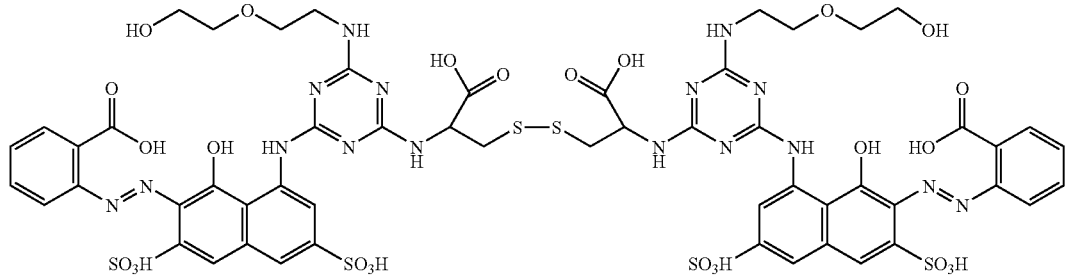
(8)
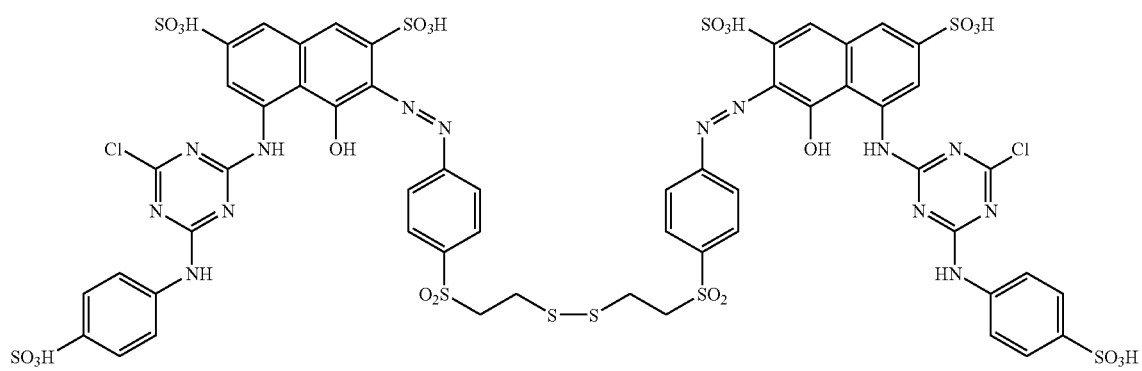
(9)
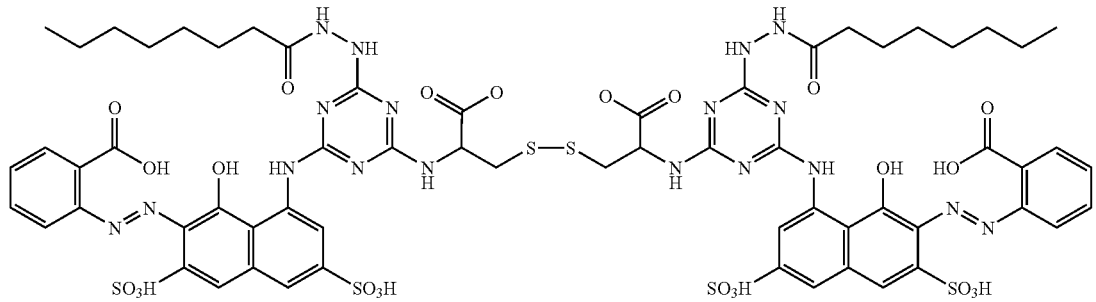
(10)
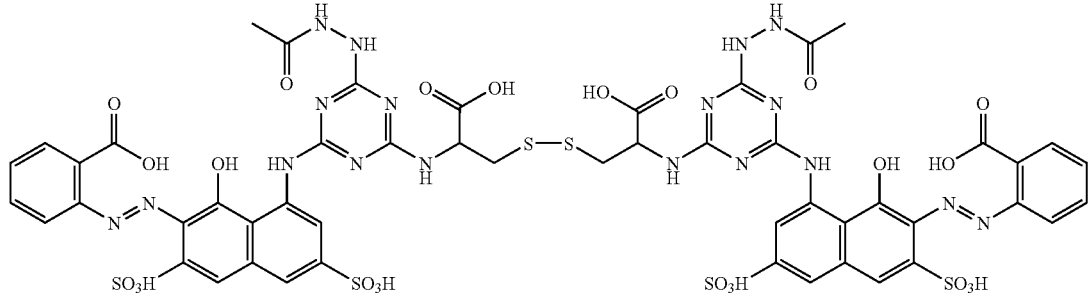
(11)
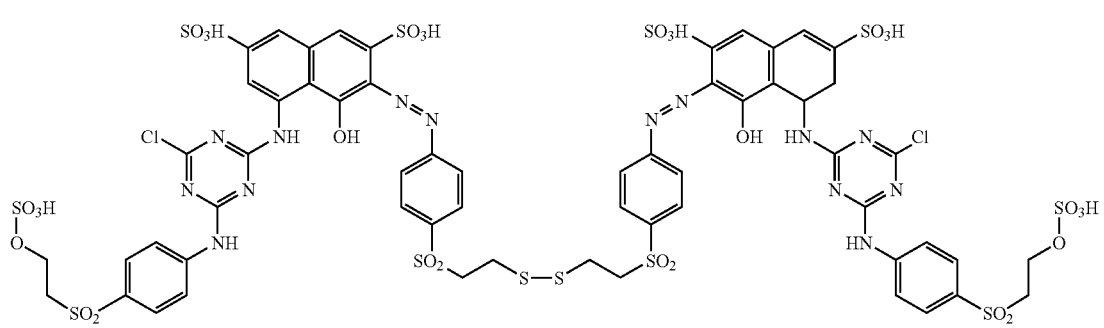

-continued
(12)
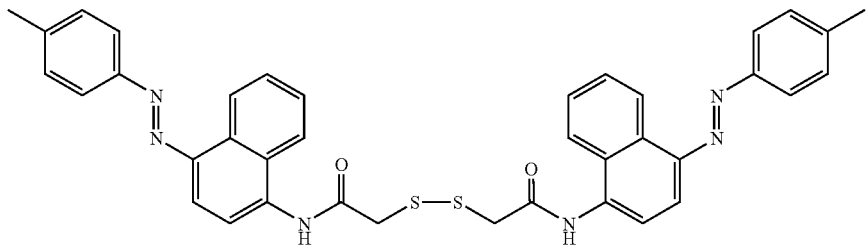
(13)
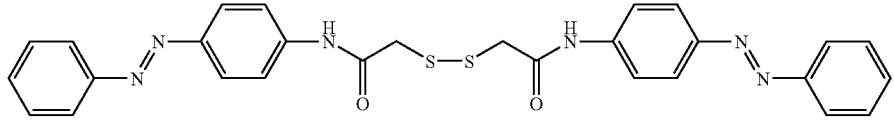
(14)
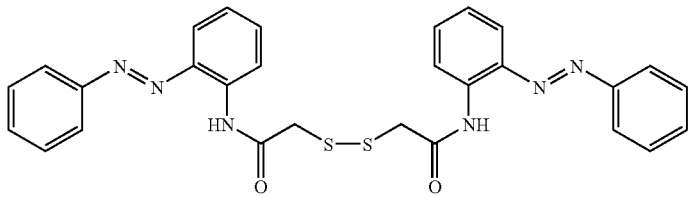
(15)
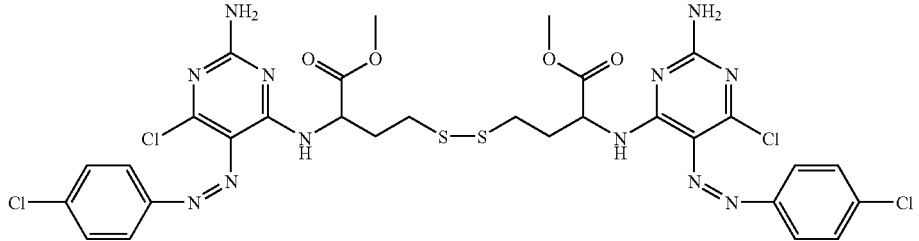
(16)
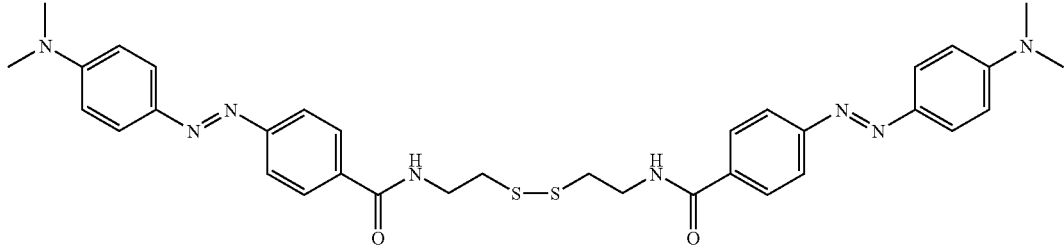
(17)
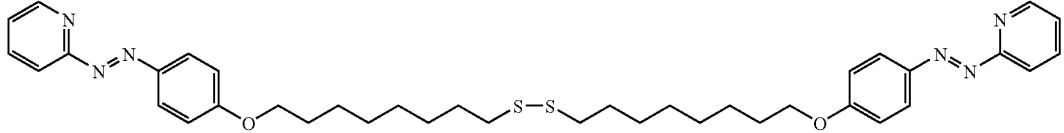
(18)
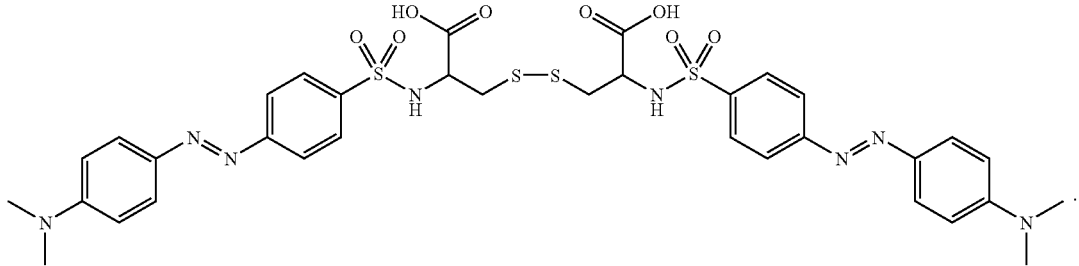

These compounds, independently of any choice of free or salified form, and their mode of preparation are known in the art.

By way of examples, mention may also be made of the following compounds which are novel and whose preparation is described herein

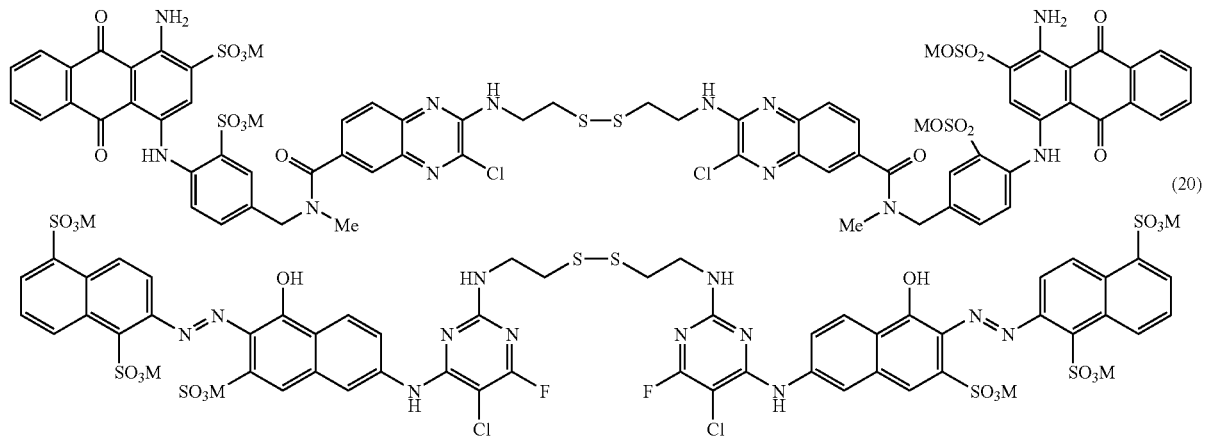

M having the same meaning as above.

In accordance with one embodiment of the present disclosure, the two radicals containing at least one chromophore A and A' comprise at least one cationic radical carried or included in or on a chromophore. By way of example, mention may be made of the compounds of the following formulae, their salts, hydrates or solvates:

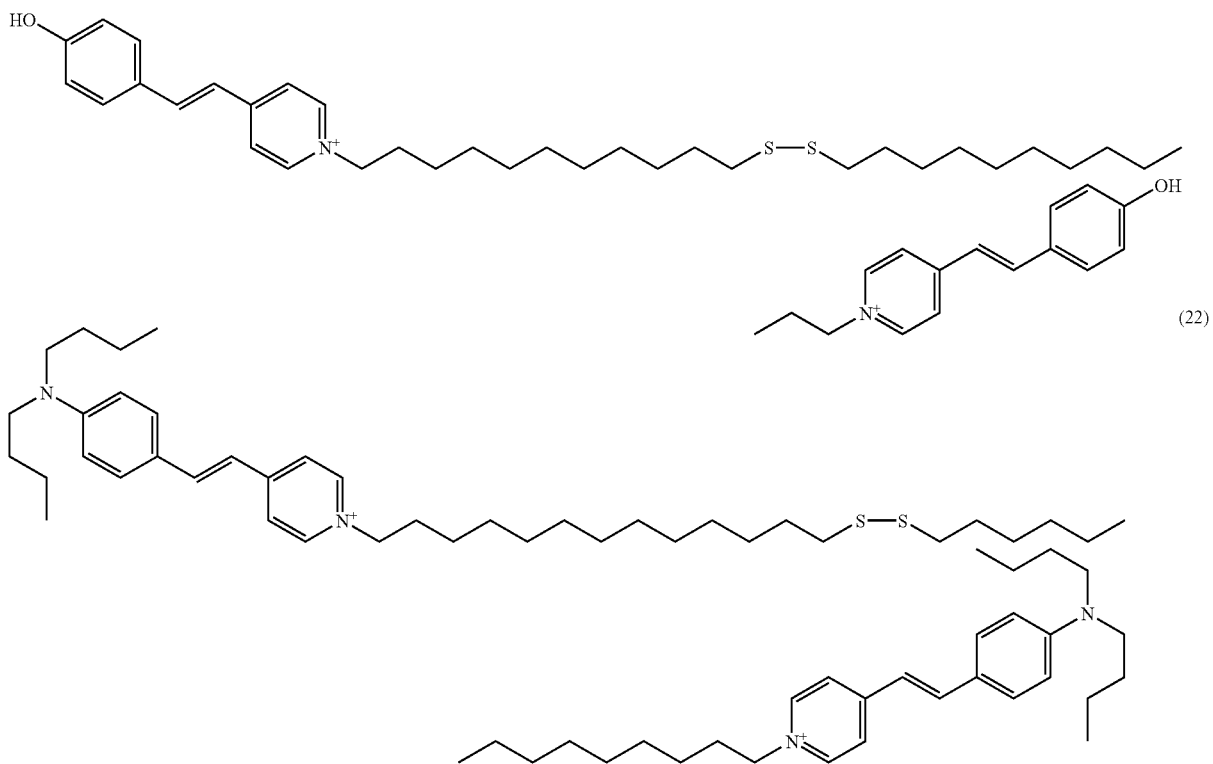

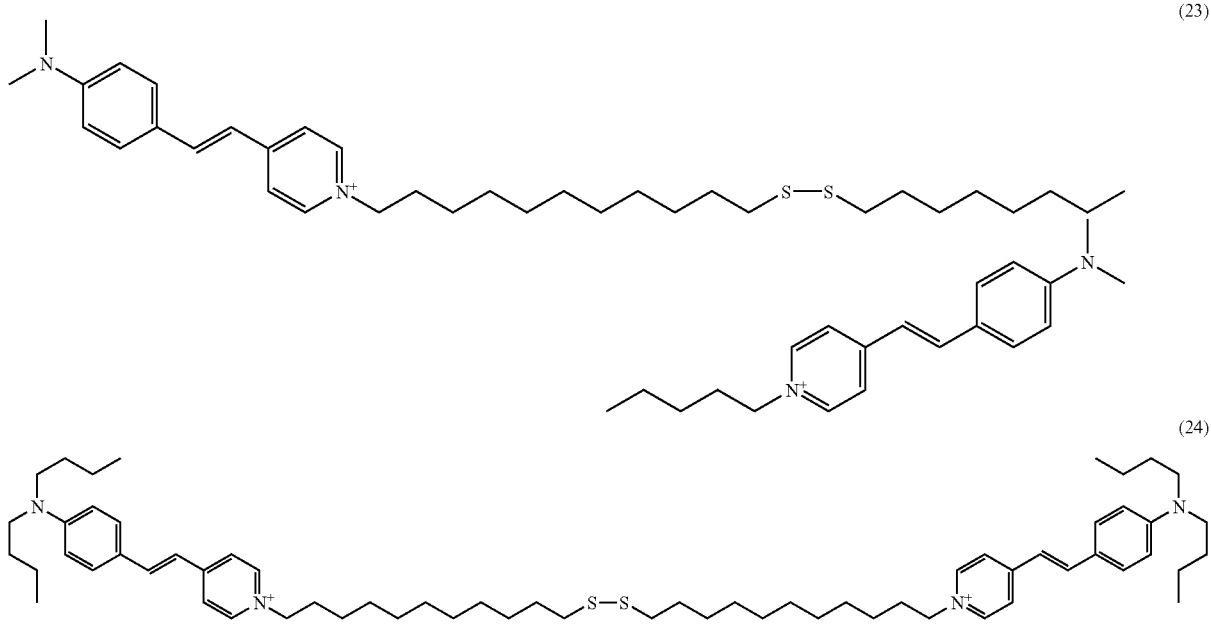

(23)

(24)

These four compounds, independently of any choice of free or salified form, and their mode of preparation are known in the art.

According to another embodiment of the present disclosure, the disulphide dye is a cationic dye comprising at least one quaternary ammonium radical and such that, in formula (I) with p equal to 1:

A is W—N=N—Ar— or —W—N=N—Ar, wherein W is chosen from a fused or nonfused, aromatic or nonaromatic heterocycle comprising a quaternary ammonium; Ar is chosen from a $C_5$ or $C_6$ aryl radical and an aromatic bicycle of the naphthyl type, which are optionally substituted with at least one halogen atom, such as chlorine or fluorine atoms; with at least one alkyl, such as $C_1$-$C_4$ alkyl, groups; with at least one hydroxyl group; with at least one alkoxy group, with at least one hydroxyalkyl group, with at least one amino or (di)alkylamino group, wherein, for example, the alkyl part may be $C_1$-$C_4$.

According to one embodiment, p=1, y=z=0, t=1 and T is —N(R)—, for example at the para-position on Ar with respect to the azo functional group.

In at least one embodiment, W is chosen from imidazolium, pyridinium, benzimidazolium, pyrazolium, and benzothiazolium which are optionally substituted with at least one identical or different $C_1$-$C_4$ alkyl radical.

Among the disulphide dyes of the present disclosure, there may be mentioned, for example, the following compounds:

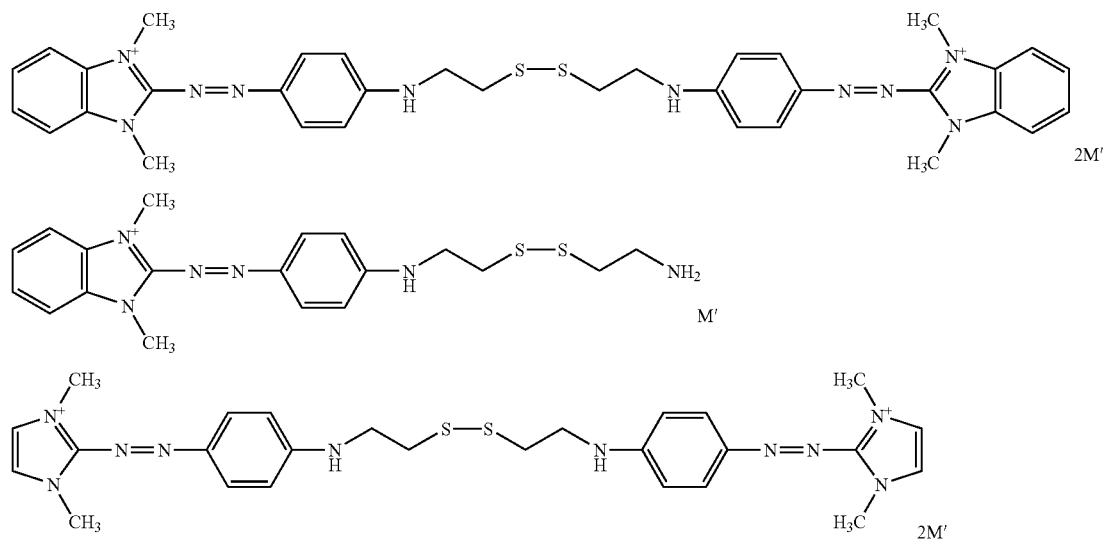

-continued

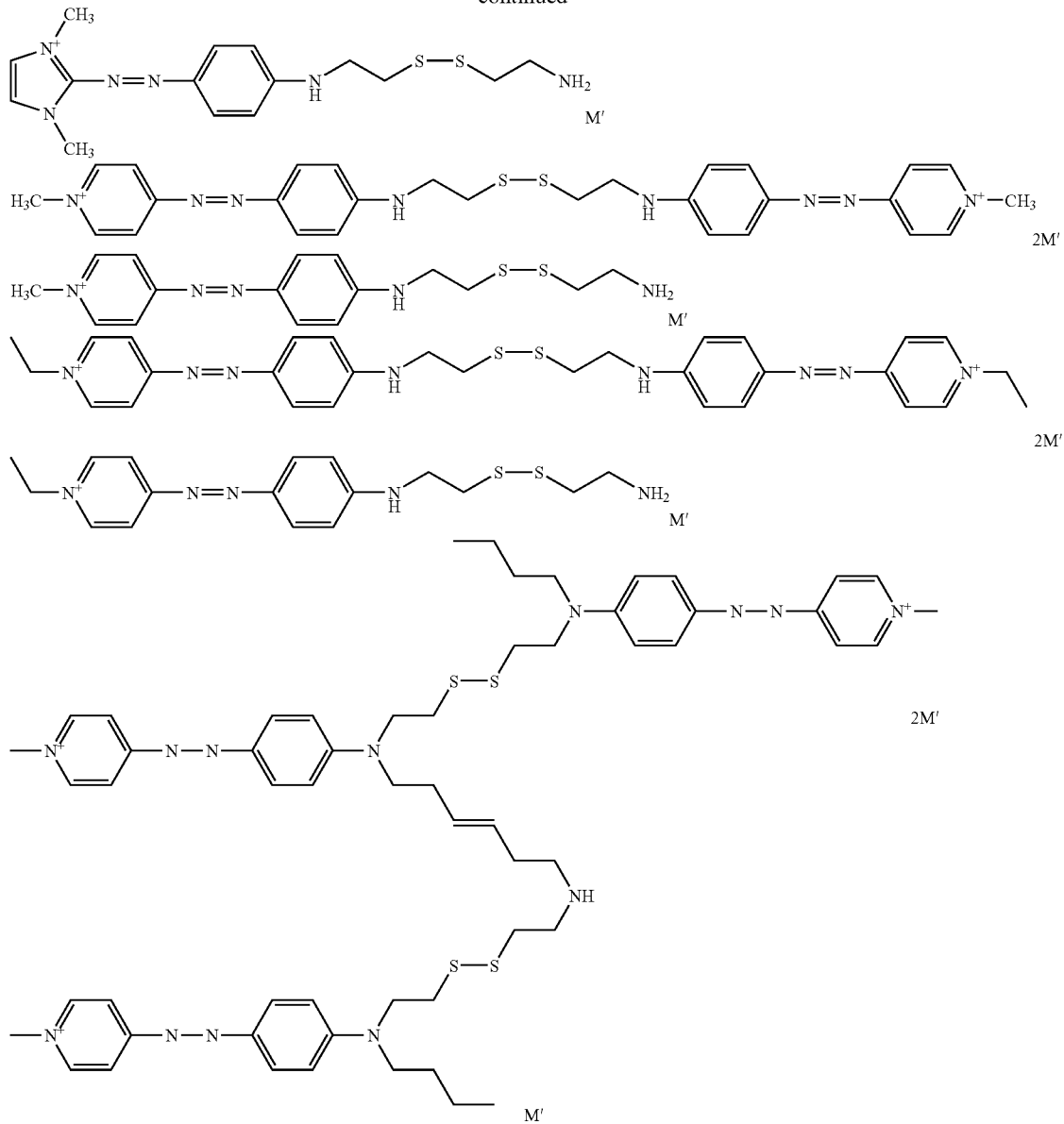

wherein M is a salt of an organic or inorganic acid.

In at least one embodiment, the salt of an organic or inorganic acid is chosen from hydrochlorides, hydrobromides, sulphates, including methyl sulphate and ethyl sulphate, citrates, succinates, tartrates, lactates, acetates, methosulphates, tosylates, benzenesulphonates, phosphates and acetates.

The disulphide dyes may be prepared according to methods known to persons skilled in the art.

According to a first embodiment, a disulphide compound comprising two, for example primary or secondary, amine functional groups can be reacted with a sufficient quantity of a "reactive chromophore" or of a compound comprising such a "reactive chromophore", in other words comprising an electrophilic functional group.

Among the "reactive chromophores", there may be mentioned the reactive dyes listed as such in the Colour Index and containing, for example, a vinylsulphone, sulphatoethylsulple;hone, mono- or dichlorotriazine, mono- or dichloropyrimidine, difluorochloropyrimidine, dichloroquinoxaline or bromovinylsulphone functional group.

Also suitable, as reactive chromophores, are the chromophore compounds comprising at least one group capable of reacting with an amine functional group to give a sulphamide group (—$SO_2$—N—) or an amide group (—CO—N—). For example, mention may be made of the groups —$SO_2$M', —COO M' (wherein M' is chosen from a hydrogen atom, an alkali metal such as sodium or potassium, an ammonium group, an ammonium group substituted with at least one identical or different, linear or branched $C_1$-$C_{10}$ alkyl group, optionally bearing at least one hydroxyl), which can be activated beforehand according to known methods as —$SO_2$Cl or —COCl group, respectively.

It is thus possible to envisage using, as reactive chromophore, the acid dyes of the Colour Index which are listed as such.

Reference may also be made to the book Advanced Organic Chemistry, March, 4th Ed, to have more details on the operating conditions used.

In the context of this first embodiment, it is possible to use chromophores comprising a labile group which is directly linked or otherwise to the chromophore and which may be substituted with an amine group, such as Cl, Br, F, O-alkyl (for example O—Me), O-aryl, O-alkylaryl (for example O-benzyl).

The disulphide dyes may also be obtained, in the context of this embodiment, using chromophores possessing an acrylate functional group (—OCO—C=C—) on which an addition reaction is performed.

In accordance with a second embodiment, the disulphide dyes may be obtained by reacting a disulphide compound with a compound bearing two carboxylic acid functional groups activated according to conventional methods (for example reaction with a carbodiimide or with thionyl chloride). The resulting product is then reacted with a chromophore bearing a nucleophilic functional group, for example of the primary or secondary amine type, or of the aliphatic or aromatic alcohol type such as phenol.

Here again, reference may be made to the book Advanced Organic Chemistry, March, 4th Ed, to have more details on the operating conditions used.

In accordance with a third embodiment, the disulphide dyes may be obtained by reaction of a compound comprising a disulphide group and two hydroxyl groups activated beforehand as leaving groups (for example mesylate, tosylate) with a chromophore bearing a nucleophilic functional group, for example of the primary, secondary or tertiary amine type, which is heteroaromatic or not, for example of the pyridine, imidazole or benzimidazole type.

In accordance with a fourth embodiment, the disulphide dyes may be obtained by controlled oxidation of dyes bearing an SH functional group.

In accordance with a a fifth embodiment, and, for example, for the preparation of the compounds corresponding to formulae (III) and (IV), the disulphide dyes may be obtained by one of embodiments one, two or three described above, using a molar quantity of disulphide reagent greater than or equal to the molar quantity of reagent containing the chromophore group.

The preparation of the disulphide dyes corresponding to formula (I) is on the other hand facilitated by the use of a molar quantity of reagent containing the chromophore group, for example a quantity greater than or equal to twice the quantity of disulphide reagent.

In accordance with a sixth embodiment, and, for example, for the preparation of compounds corresponding to formula (I) and in which the two groups A, on the one hand, and X, on the other hand, are different, the disulphide compounds may be obtained from disulphide compounds corresponding to formula (IV).

Dyeing Compositions and Methods

The dyeing composition useful in the method of the present disclosure may comprise at least one disulphide dye chosen from dyes of formulae (I), (II), (III) or (IV).

The at least one disulphide dye may be present in the composition in an amount ranging from 0.001 to 50% relative to the total weight of the composition. In at least one embodiment, this amount ranges from 0.005 to 20% by weight, such as from 0.01 to 5% by weight relative to the total weight of the composition.

The dyeing composition may additionally comprise at least one direct dye different from the disulphide dyes of formulae (I), (II), (III) or (IV). These additional direct dyes are, for example, chosen from the direct dyes listed earlier, such as from the neutral, acidic or cationic nitrobenzene direct dyes, the neutral, acidic or cationic azo direct dyes, the tetraazapentamethine dyes, the neutral, acidic or cationic quinone, e.g., anthraquinone dyes, the azine direct dyes, the triarylmethane direct dyes, the indoamine direct dyes and the natural direct dyes.

Among the tetraazapentamethine-type dyes which can be used, mention may be made of the following compounds shown in the table below, wherein An is chosen from, in general, an organic or inorganic anion as defined above:

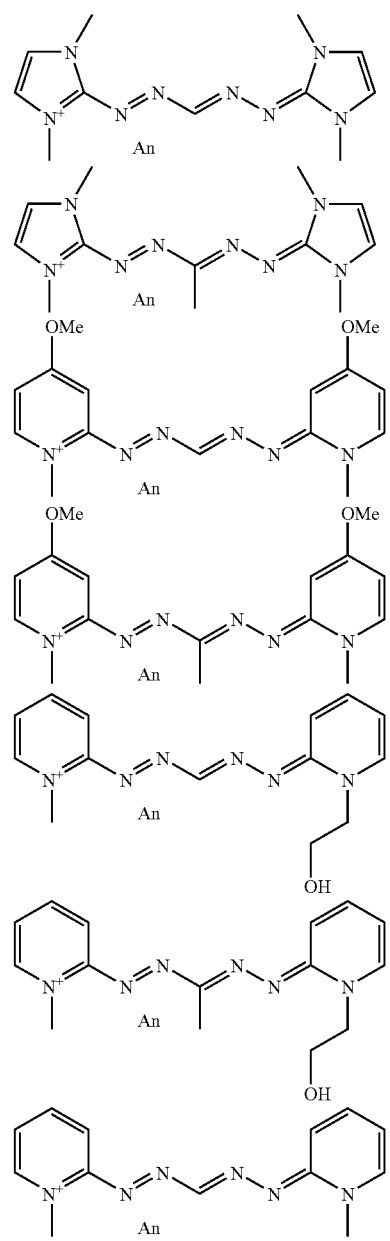

-continued

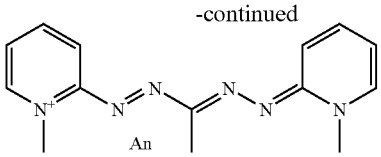

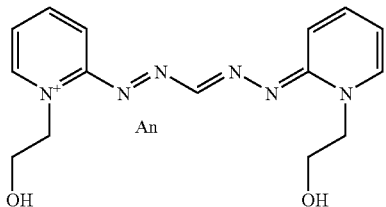

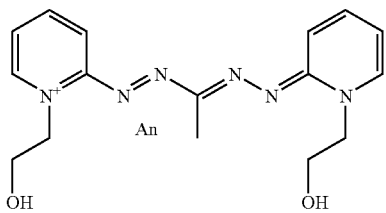

Among the natural direct dyes, mention may be made of lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes, and, for example, poultices or extracts based on henna.

The dyeing composition may further comprise at least one oxidation base and/or at least one coupler conventionally used for dyeing keratin fibers.

Among the oxidation bases, mention may be made of para-phenylenediamines, bisphenylalkylenediamines, para-aminophenols, bis-para-aminophenols, ortho-aminophenols, heterocyclic bases and their addition salts.

Among the couplers, there may be mentioned meta-phenylenediamines, meta-aminophenols, meta-diphenols, naphthalene couplers, heterocyclic couplers and their addition salts.

The coupler(s) is (are) each generally present in an amount ranging from 0.001 to 10% by weight relative to the total weight of the dyeing composition, such as from 0.005 to 6%.

The oxidation base(s) present in the dyeing composition is (are) in general each present in an amount ranging from 0.001 to 10% by weight relative to the total weight of the dyeing composition, such as from 0.005 to 6% by weight.

In general, the addition salts of the oxidation bases and couplers which can be used in the context of the present disclosure are chosen, for example, from addition salts with an acid, such as the hydrochlorides, hydrobromides, sulphates, citrates, succinates, tartrates, lactates, tosylates, benzenesulphonates, phosphates and acetates, and addition salts with a base, such as the alkali metal hydroxides such as sodium hydroxide or potassium hydroxide, aqueous ammonia, amines or alkanolamines.

The appropriate medium for dyeing, also called the dye support, is a cosmetic medium which generally comprises water or a mixture of water and at least one organic solvent. As organic solvent, mention may be made for example of lower $C_1$-$C_4$ alkanols such as ethanol and isopropanol; polyols and polyol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, and mixtures thereof.

The solvents, when they are present, may be present in an amount ranging from 1 to 40% by weight relative to the total weight of the dyeing composition, such as from 5 to 30% by weight.

The dyeing composition may also comprise at least one adjuvant conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickening agents, such as anionic, cationic, nonionic and amphoteric associative polymeric thickeners, antioxidants, penetration agents, sequestering agents, perfumes, buffers, dispersing agents, conditioning agents such as for example modified or unmodified, volatile or nonvolatile silicones, film forming agents, ceramides, preservatives and opacifiers.

The above adjuvants are generally present in an amount for each of them of from 0.01 to 20% by weight relative to the weight of the composition.

The composition may also comprise at least one other additional disulphide compound different from that corresponding to formulae (I) to (IV) detailed above. As a guide, the disulphide may be chosen from compounds comprising at least one fatty chain, such as at least one saturated or unsaturated, linear or branched $C_5$-$C_{30}$ hydrocarbon chain which is optionally substituted with a heteroatom and optionally interrupted by a neutralized or nonneutralized carboxyl group. By way of example of compounds of this type, mention may be made of the dimers of thioglycolic acid and its derivatives of the $CH_3$—$(CH_2)_{17}$—S—S—$(CH_2)_{17}$—$CH_3$ or $CH_3$—$(CH_2)$—S—S—$(CH_2)_{10}$—$CH_3$ type.

If it is present, the at least one additional disulphide compound is present in an amount ranging from 0.001 to 10% by weight relative to the weight of composition.

Of course, persons skilled in the art will be careful to choose this or these optional additional compounds such that the advantageous properties intrinsically attached to the dyeing composition in accordance with the invention are not, or not substantially, impaired by the addition(s) envisaged.

The pH of the dyeing composition may range from 3 to 14, such as from 5 to 11. It may be adjusted to the desired value by means of acidifying or alkalinizing agents customarily used for dyeing keratin fibers, or alternatively with the aid of conventional buffer systems.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid and sulphonic acids.

Among the alkalinizing agents, there may be mentioned, by way of example, aqueous ammonia, alkali metal carbonates, alkanolamines such as mono-, di- and triethanolamines and derivatives thereof, sodium or potassium hydroxides and compounds of the following formula (A):

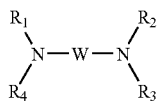

(A)

in which W is a propylene residue optionally substituted with a hydroxyl group or a $C_1$-$C_4$ alkyl radical; $R_1$, $R_2$, $R_3$ and $R_4$, which are identical or different, are chosen from a hydrogen atom, a $C_1$-$C_4$ alkyl radical and a $C_1$-$C_4$ hydroxyalkyl radical.

The dyeing composition may be provided in various forms, such as in the form of a liquid, a cream, a gel, or in any other appropriate form for dyeing keratin fibers, such as the hair.

According to one embodiment, the method of the invention comprises a pretreatment with a reducing agent capable of reducing the disulphide bond. The reducing agent is chosen, for example, from thiols, for example thioglycolic acid, cysteine, homocysteine, thiolactic acid, the salts of these thiols, phosphines, bisulphite and sulphites.

This reducing agent may also be chosen from borohydrides and derivatives thereof, such as, for example, the borohydride, cyanoborohydride, triacetoxyborohydride and trimethoxyborohydride salts: sodium, lithium, potassium, calcium and quaternary ammonium (tetramethylammonium, tetraethylammonium, tetra-n-butylammonium, benzyltriethylammonium) salts; catecholborane.

This pretreatment may be of a short duration, from 0.1 second to 30 minutes, for example from 0.1 second to 5 minutes, with a reducing agent as mentioned above.

The application of the dyeing composition is generally carried out at room temperature. It may however be carried out at temperatures ranging from 20 to 180° C.

According to one embodiment, the reducing agent is added to the dyeing composition at the time of use.

According to another embodiment, the application of the dyeing composition may be followed by a short reducing step of 0.1 second to 30 minutes, such as from 0.1 second to 5 minutes, with a reducing agent of the thiol or borohydride type as described above.

According to another embodiment, the dyeing composition may comprise at least one oxidizing agent; the composition is then said to be "ready-to-use."

In at least one embodiment, the composition is obtained by mixing the composition according to the disclosure with an oxidizing composition before application to the keratin materials to be treated.

The oxidizing agent may be any oxidizing agent conventionally used in the field. Thus, it may be chosen from hydrogen peroxide, urea peroxide, alkali metal bromates, persalts such as perborates and persulphates, and enzymes, among which mention may be made of peroxidases, oxidoreductases containing 2 electrons such as uricases, and oxygenases containing 4 electrons such as laccases. In at least one embodiment, the oxidizing agent is hydrogen peroxide.

The amount of oxidizing agent in the composition ranges from 1 to 40% by weight relative to the weight of the ready-to-use composition, such as from 1 to 20% by weight relative to the weight of the ready-to-use composition.

Generally, the oxidizing composition used is an aqueous composition and may be in the form of a solution or also an emulsion.

Customarily, the dyeing composition, free of oxidizing agent, is mixed with 0.5 to 10 equivalents by weight of the oxidizing composition.

It should be noted that the pH of the ready-to-use composition is, for example, from 4 to 12, such as from 7 to 11.5.

The application of the dyeing composition may be followed by an oxidizing post-treatment, or by a conditioning post-treatment optionally combined with an oxidizing post-treatment.

Multi-Compartment Kits and Devices

Also disclosed herein is a multicompartment device or dyeing "kit" in which a first compartment comprises a dyeing composition comprising at least one disulphide dye of formulae (I), (II), (III) or (IV), and a second compartment comprises a reducing agent capable of reducing the disulphide bond of the dye.

One of these compartments may additionally comprise at least one other dye chosen from direct dyes and oxidation dyes provided that the disulphide dye which is useful herein and the at least one other dye are not in the same compartments of the kit.

The disclosure also relates to a multicompartment device in which a first compartment comprises a dyeing composition comprising at least one disulphide dye of formulae (I), (II) or (III) or (IV); a second compartment comprises a reducing agent capable of reducing the disulphide bond of the dye; a third compartment comprises an oxidizing agent.

Each of the abovementioned devices may be equipped with a means which makes it possible to deliver the desired mixture to the hair, for example such as the devices described in Patent FR 2 586 913.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

The examples which follow serve to illustrate the invention without however being limiting.

EXAMPLES

Examples of Synthesis

Example 1

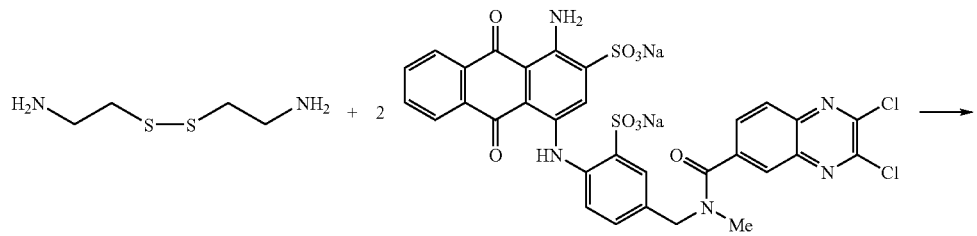

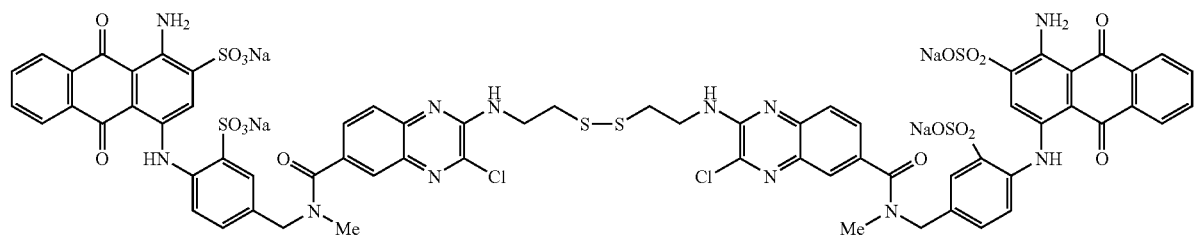

A solution composed of 500 mg of cystamine dihydrochloride (2.22 mmol) and 20 ml of 0.05M borate buffer pH 9 was prepared and was brought to pH 9 by adding molar sodium hydroxide. 4.6 grams of Reactive Blue 44 [Cas number 12225-56-8] at 60% purity (that is 4.44 mmol) were added to this solution. The mixture was stirred for 18 hours at room temperature, the precipitated dye was filtered off and dried. 1.67 g of blue dye (I) were recovered.

Example 2

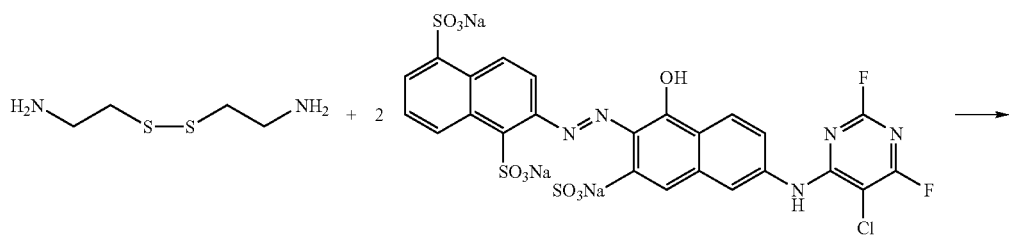

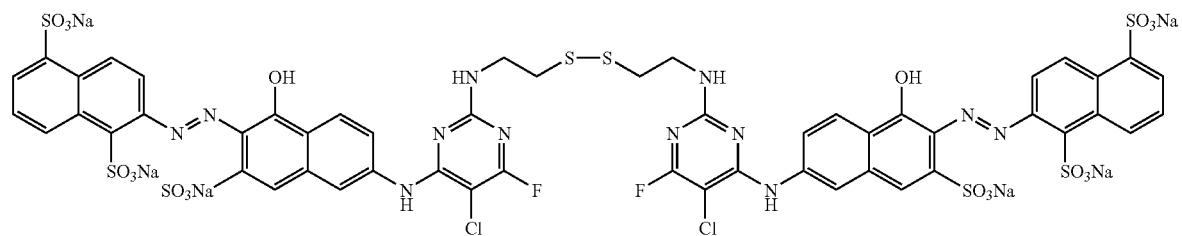

A solution composed of 500 mg of cystamine dihydrochloride (2.22 mmol) and 20 ml of 0.05M borate buffer pH 9 was prepared and was brought to pH 9 by adding molar sodium hydroxide. 6.23 grams of Reactive Orange 64 [Cas number 61901-80-2] at 50% purity (that is 4.44 mmol) were added to this solution. The mixture was stirred for 18 hours at room temperature, the precipitated dye was filtered off and dried. 2.03 g of orange dye (II) were recovered.

Example 3

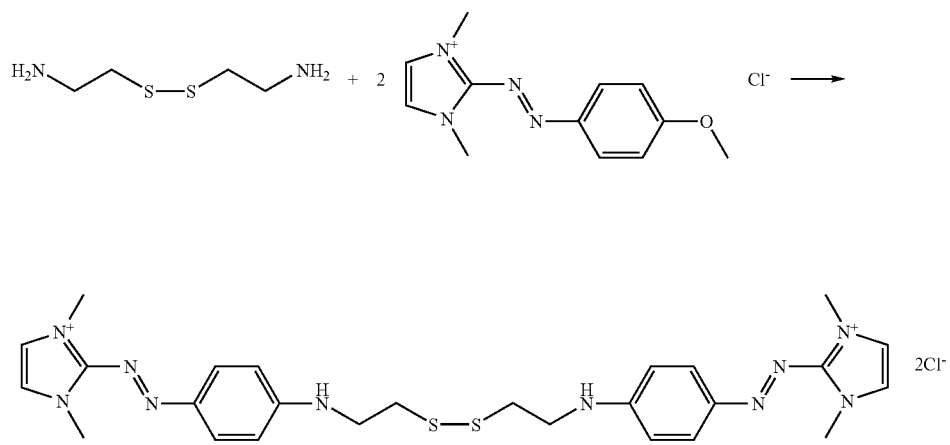

The cystamine base (552.2 mg; 3.62 mmol) obtained from cystamine dihydrochloride by addition of sodium hydroxide and extraction with ethyl acetate was solubilized in 2 ml of pentanol. 2-[(4-Methoxyphenyl)diazenyl]-1,3-dimethyl-1H-imidazol-3-ium chloride (2.42 m; 9.1 mmol), in suspension in 80 ml of dichloromethane, was added. The mixture was heated to 50° C. and kept stirring for 1 hour. It was concentrated under vacuum (removal of the dichloromethane), 20 ml of water were added and the reaction mixture was kept for an additional hour at 50° C. It was then cooled and poured over 50 ml of pentanol; a red precipitate appeared which was filtered off and washed with acetone and then dried under vacuum. 1.1 g of a dark red powder were thus obtained, which powder was in conformity with the above structure.

Example 4

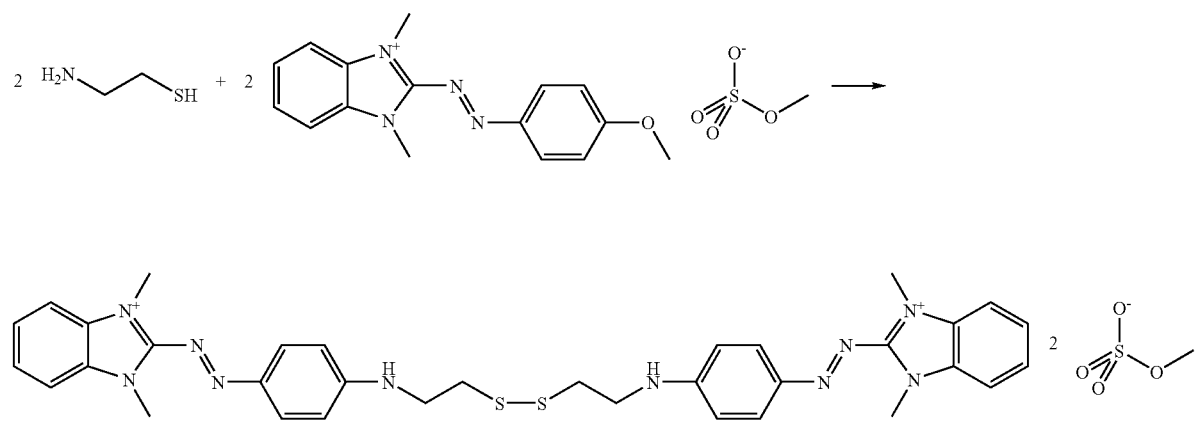

The cystamine base (110.2 mg; 0.73 mmol) was solubilized in 2 ml of methanol. 2-[(4-Methoxyphenyl)diazenyl]-1,3-dimethyl-1H-imidazol-3-ium methyl sulphate (600 mg; 1.53 mmol), in suspension in 10 ml of dichloromethane, was added. The mixture was heated to 35° C. and kept stirring for 2 hours in the presence of oxygen (air). At the end of the process, 200 ml of ethyl acetate were introduced.

The precipitate obtained was filtered off. A black powder was obtained (278 mg) which predominantly contained the expected product.

Example 5

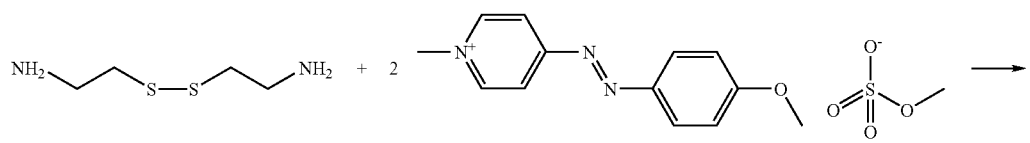

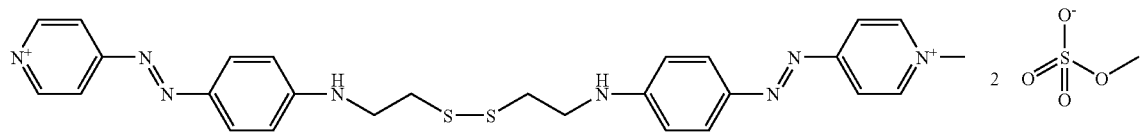

4.18 mg of 4-[(E)-(4-methoxyphenyl)diazenyl]-1-methylpyridinium methyl sulphate were dissolved in 275 ml of dichloromethane and added dropwise to a solution of 1.25 g of cystamine in 2 ml of pentanol, at 50° C. (the dichloromethane distilled; the reaction mixture thus obtained was homogeneous and concentrated). After stirring for 24 h, the mixture was concentrated under vacuum. The oil obtained was mixed with acetone and 100 ml of celite. The paste obtained was washed with acetone, dichloromethane and ethyl acetate. The expected product was then desorbed from the celite by extraction with water. The aqueous solution obtained was concentrated under vacuum. 2 g of a black-red solid were thus recovered. Analyses show that this solid predominantly contained the expected product (m/z:272; λ max 520).

Example 6

1 g of 1-bromo-2-[(2-bromoethyl)disulphanyl]ethane and 2.14 g of 2-((2-hydroxyethyl)-{4-[(E)-pyridin-4-yldiazenyl]phenyl}amino)ethanol were dissolved in 5 ml of dimethylformamide. The mixture was stirred and heated at 80° C. for 4 h. After cooling the mixture, 200 ml of acetone were added. A black oil separated upon settling (1.94 g). This oil was purified by water/butanol liquid extraction and after evaporation of the aqueous phases, 1.77 g of a black paste were recovered. Analyses show that this oil predominantly contained the expected product (m/z:346; λ max 548 nm).

Example 7

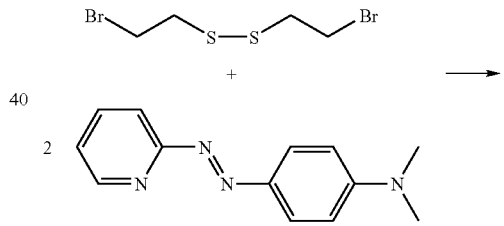

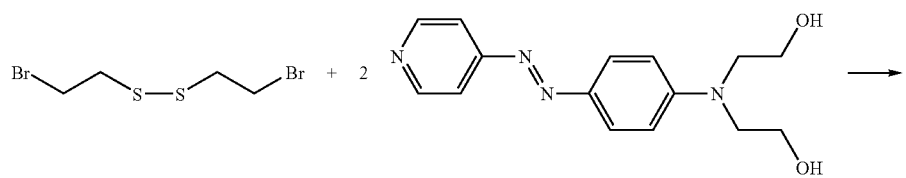

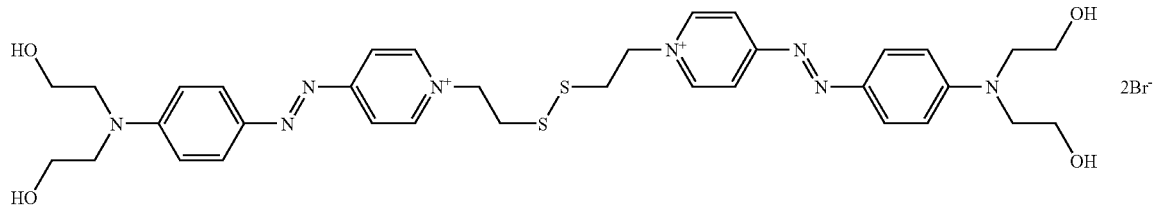

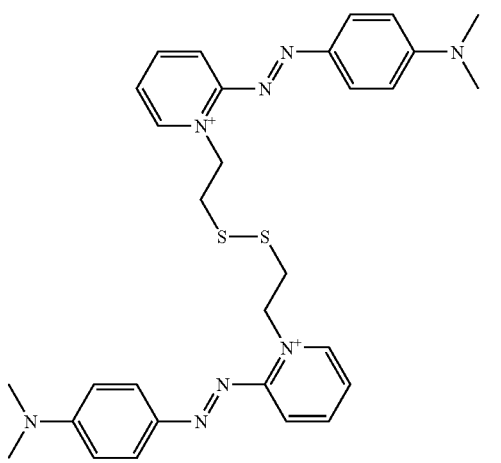

1 g of 1-bromo-2-[(2-bromoethyl)disulphanyl]ethane and 1.7 g of N,N-dimethyl-4-[(Z)-pyridin-2-yldiazenyl]aniline were mixed in 5 ml of dimethylformamide. The mixture was stirred and heated at 80° C. for 4 h. After cooling the reaction mixture, 200 ml of acetone wee added. A precipitate formed, it was filtered off, washed with three times 100 ml of acetone and then dried. The product obtained was solubilized in 50 ml of a 1:1 water/ethanol mixture and re-precipitated by addition of acetone. The precipitate was filtered off and then dried. 1.34 g of a black-purple powder were thus recovered. Analyses were in conformity with the structure of the expected product (m/z 286; λ max:534 nm).

Example 8

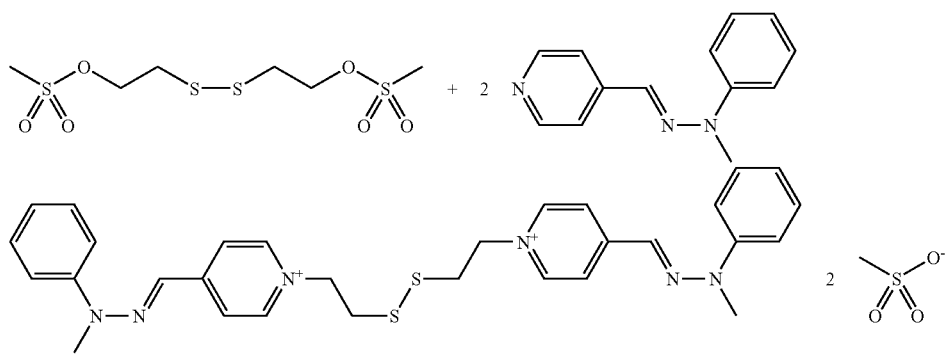

11.38 g of 2-({2-[(methylsulphonyl)oxy]ethyl}disulphanyl)ethyl methanesulphonate and 15.50 g of 4-{(E)-[methyl(phenyl)hydrazono]methyl}pyridine were mixed in 10 ml of dimethylformamide. The heterogeneous mixture thus obtained was heated and stirred at 80° C. for 4 h. The dimethylformamide was distilled off under vacuum. The solid obtained was purified by water/butanol liquid chromatography. 7.64 g of a yellow solid were recovered after evaporation of the solvent. Analyses were in conformity with the structure of the expected product (m/z:271; λ max 422 nm).

Example 9

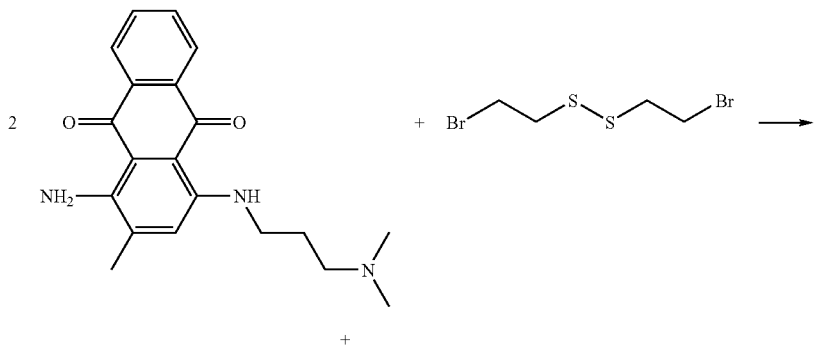

-continued

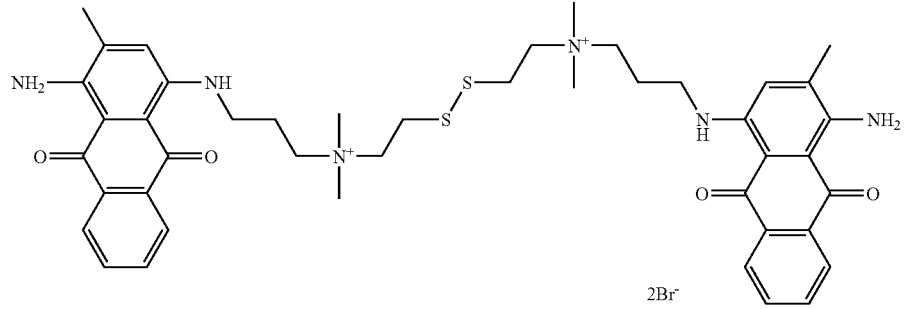

500 mg of 1-bromo-2-[(2-bromoethyl)disulphanyl]ethane and 1.405 g of 1-amino-4-{[3-(dimethylamino)propyl]amino}-2-methylanthra-9,10-quinone were dissolved in 5 ml of dimethylformamide. The mixture thus obtained was stirred and heated at 80° C. for 8 h. The mixture was cooled and poured over 200 ml of acetone. The precipitate obtained was filtered off and washed with 3 times 100 ml of acetone. The solid obtained was solubilized in 50 ml of a 1:1 water/ethanol mixture and then reprecipitated by addition of acetone. The precipitate was filtered off and then dried in an oven (66° C.). 465 mg of a black powder were recovered. Analyses are in conformity with the structure of the expected product (m/z: 397; λ max 564 and 610 nm).

Examples of Dyeing

Example 10

Step 1: Pretreatment with a Dilute Reducing Solution

Natural, permanently waved or bleached locks of grey hair which were 90% white were impregnated with a reducing solution for permanent waving (Dulcia Vital No. 2 marketed by L'Oreal Professionnel diluted ½ in deionized water) for three minutes and then rinsed with running water for 30 seconds.

Step 2: Application of the Dye

A solution of the disulphide dye of Example 2 above at 1% w/w in a medium buffered to pH 9 (0.05M borate) was applied to hair pretreated according to Step 1 described above, at the rate of 5 g of solution per gram of hair, for 10 minutes at room temperature.

The hair was thoroughly rinsed with running water and then dried.

The locks were evaluated before and after dyeing in the L*a*b* system by means of a Minolta® CM 2002 spectrophotometer (Illuminant D65).

In the L*a*b* system, the three parameters denote respectively the intensity (L*), the shade (a*) and the saturation (b*). According to this system, the higher the value of L, the lighter and less intense the color. Conversely, the lower the value of L, the darker and more intense the color. a* and b* indicate two axes of colors, a* indicates the green/red color axis and b* the blue/yellow color axis.

The results are grouped together in the table below:

| Type of hair | L | a | b | Color |
|---|---|---|---|---|
| Natural grey hair | 48.13 | 22.20 | 24.30 | orange |
| Permanently waved grey hair | 43.22 | 27.05 | 28.72 | orange |
| Bleached hair | 40.49 | 43.09 | 41.00 | orange |

Example 11

Step 1: Pretreatment with a Dilute Reducing Solution

Natural, permanently waved or bleached locks of grey hair which were 90% white were immersed or simply impregnated with a reducing solution: thioglycolic acid at a concentration of 0.05; 0.2; 1 molar (pH brought to 8.5; immersion in the solution for 10 min).

Step 2: Application of the Dye

An aqueous formula of the disulphide dye of Example 3 above at $10^{-3}$ mol/100 g of dye in a medium buffered to pH 9 (0.05M borate) was applied to hair pretreated according to step 1 described above, at the rate of 5 g of solution per gram of hair, for 20 minutes at room temperature.

The hair was thoroughly rinsed with running water and then dried.

Locks were also treated with the aqueous formula containing the disulphide dye of Example 3 without a pretreatment step with a reducing solution.

The locks were evaluated before and after dyeing in the L*a*b* system, according to the method of Example 5.

The dyed locks were subjected to 12 shampooings according to a cycle which comprises wetting the locks with water, washing with shampoo, rinsing with water followed by drying.

The color of the locks before and after 12 washes was evaluated in the L*a*b* system. The variation in color before and after washing was measured by ΔE according to the equation above starting with the L0*a0*b0* values for the dyed locks and the L*a*b* values obtained after 12 shampooings.

$$\Delta E = \sqrt{(L^*-L_o^*)^2+(a^*-a_o^*)^2+(b^*-b_o^*)^2}$$

The higher the ΔE value, the greater the difference in color before and after washings, and in the present case, the lower the fastness of the coloration to shampooing.

The results are grouped together in the table below:

| | Application without reducing treatment | | | | |
|---|---|---|---|---|---|
| Type of hair | * | L* | a* | b* | DE* |
| Natural grey hair | 0 | 34.1 | 32.5 | 15.1 | |
| Natural grey hair | 3 | 32.3 | 34.3 | 15.4 | 2.5 |
| Natural grey hair | 12 | 41.9 | 34.0 | 13.2 | 8.2 |

*Number of shampooings carried out on the locks before the measurement of color

| Application with prior reducing treatment (step 1) | | | | | |
|---|---|---|---|---|---|
| Type of hair | * | L* | a* | b* | DE* |
| Natural grey hair | 0 | 28.826 | 26.217 | 17.448 | |
| Natural grey hair | 3 | 30.576 | 24.596 | 15.692 | 2.9 |
| Natural grey hair | 12 | 31.566 | 29.86 | 17.108 | 4.6 |

*Number of shampooings carried out on the locks before the measurement of color

These results show that the composition of the invention had good wash-fastness, in particular when the dyeing method comprises a reducing pretreatment.

What is claimed is:

1. A method for dyeing human keratin fibers comprising applying to the fibers a dyeing composition comprising, in an appropriate cosmetic medium, at least one disulphide dye chosen from the dyes of the following formulae (I), (II), (III) or (IV):

$$A-(X)_p-C_{sat}-S-S-C_{sat}-(X)_p-A \quad (I)$$

$$A'-(X)_p-C_{sat}-S-S-C_{sat}-(X)_p-A' \quad (II)$$
$$\phantom{A'-(X)_p-C_{sat}}\underline{\phantom{---}(V)_v\phantom{---}}$$

$$A-(X)_p-C'_{sat}-S-S-C_{sat} \quad (III)$$
$$\phantom{A-(X)_p-}\underline{\phantom{---}(V')_{v'}\phantom{--}}$$

$$A-(X)_p-C_{sat}-S-S-C_{sat}-(X)_p-D \quad (IV)$$

their salts, isomers and solvates, in which formulae:
   A and A', which are identical or different, are chosen from radicals compositing at least one cationic or noncationic chromophore;
   V and V', which are identical or different, are chosen from bridging groups;
   v and v', which are identical or different, are 0 or 1;
   X, which are identical or different, are chosen from saturated or unsaturated, linear or branched $C_1$-$C_{30}$ hydrocarbon chains optionally interrupted and/or optionally terminated at one or both ends by at least one divalent group, chosen from:
      —N(R)—, —N$^+$(R)(R)—, —O—, —S—, —CO—, —SO$_2$— with R, which are identical or different, being chosen from hydrogen, a $C_1$-$C_4$ alkyl radical, a hydroxyalkyl radical and a aminoalkyl radical;
      an optionally substituted, saturated or unsaturated, fused or nonfused, aromatic or nonaromatic (hetero)cyclic radical optionally comprising at least one identical or different heteroatom;
   the coefficient p is equal to 0 or 1;
   $C_{sat}$, $C'_{sat}$, which are identical or different, are chosen from optionally substituted, optionally cyclic, linear or branched $C_1$-$C_{18}$ alkylene chains;
   D is a radical chosen from hydroxyl, hydroxyalkyl, alkoxy, carboxyl, carboxylate, amino, alkylamino and dialkylamino radicals.

2. A method according to claim 1, wherein in formulae (I), (II), (III) or (IV), when p is equal to 1, X represents the following sequence:

-(T)$_t$-(Y)$_y$-(Z)$_z$- the sequence being linked in formulae (I), (II), (III) or (IV) as follows:

—C$_{sat}$(or C'$_{sat}$)-(T)$_t$-(Y)$_y$-(Z)$_z$-(A or A'); in which
   T is chosen from at least one radical chosen from —SO$_2$—, —O—, —S—, —N(R)—, —N+(R)(R)—CO—, wherein R is chosen from a hydrogen atom, a $C_1$-$C_4$ alkyl radical and a $C_1$-$C_4$ hydroxyalkyl radical, and mixtures thereof;
the coefficient t is equal to 0 or 1;
Y is chosen from:
   a radical chosen from —(CH$_2$)$_2$—SO$_2$—;
   —CH$_2$—CHR—CO—NR'— wherein R, R', which are identical or different, are chosen from a hydrogen atom, and a $C_1$-$C_4$ alkyl radical,
   a group chosen from groups of formula (a), (a') and (a"):

(a)

(a')

(a")

in which
   B is chosen from —N—, —CR$_a$, wherein R$_a$ is chosen from a hydrogen atom, a halogen atom chosen from chlorine and fluorine, a nitro group, and a pyridinium group which is optionally substituted;
   R' is chosen from a hydrogen atom and a $C_1$-$C_4$ alkyl radical
   R'$_a$ is chosen from:
      a hydrogen atom
      a halogen atom chosen from chlorine and fluorine
      a pyridinium group which is optionally substituted with at least one group R$_c$, it being possible for R$_c$ to be a $C_1$-$C_4$ alkyl group, a halogen atom, a carboxyl group —COOM (wherein M is chosen from a hydrogen atom, an alkali metal, an ammonium group, an ammonium group substituted with at least one linear or branched, identical or different $C_1$-$C_{18}$ alkyl radical, optionally bearing at least one hydroxyl group); an ester group —COOR$_d$ wherein R$_d$ is a $C_1$-$C_4$ alkyl radical; an amide group —CON(R$_d$)$_2$ wherein R$_d$, which are identical or different, are chosen from a hydrogen atom and a $C_1$-$C_4$ alkyl radical;
      a hydroxyl group an group chosen from amino, alkylamino and dialkylamino groups, wherein the alkyl groups thereof are identical or different $C_1$-$C_{18}$ alkyl groups which are linear or branched, optionally interrupted by a heteroatom chosen from N, O, S, and which are optionally substituted with at least one hydroxyl group, a group NHNHCOR where R is a linear or branched $C_1$-$C_{10}$ alkyl group a group of the following formula (b):

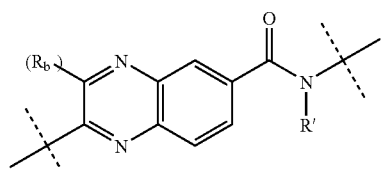

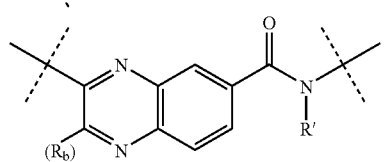

in which

R' is chosen from a hydrogen atom and a $C_1$-$C_4$ alkyl radical, $R_b$ is chosen from a chlorine atom an amino, alkylamino or dialkylamino group, the alkyl groups thereof bring identical or different $C_1$-$C_{18}$ alkyl groups which are linear or branched, optionally interrupted by a heteroatom chosen from N, O, S, and which are optionally substituted with at least one hydroxyl group a saturated or unsaturated nitrogen-containing heterocycle which may be substituted an arylamino group;

y is equal to 0 or 1;

Z is chosen from

—$(CH_2)_M$— wherein m is an integer from 1 to 8

—$(CH_2CH_2O)_q$— or —$(OCH_2CH_2)_q$— in which q is an integer from 1 to 15 an aryl, alkylaryl or arylalkyl radical whose alkyl radical is $C_1$-$C_4$, wherein the radical is optionally substituted with at least one group $SO_3M$ wherein M is chosen from a hydrogen atom, an alkali metal, an ammonium group and an ammonium group substituted with at least one identical or different, linear or branched $C_1$-$C_{18}$ alkyl radical optionally bearing at least one hydroxyl group, and z is equal to 0 or 1.

3. A method according to claim 1, wherein Y is chosen from:

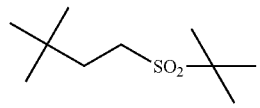

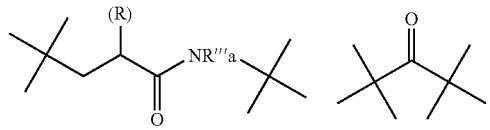

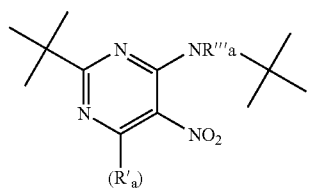

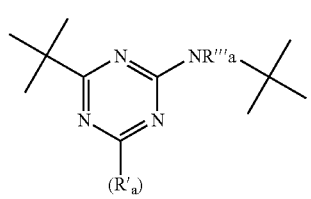

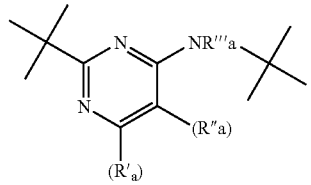

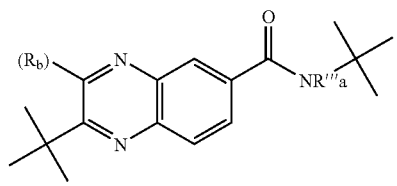

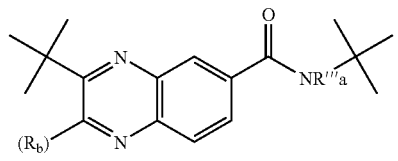

in which the radicals R, $R'_a$ and $R_b$ are defined as in claim 1;

$R''_a$ has the same definition as $R'_a$, independently of each other;

$R'''_a$ is chosen from a hydrogen atom and an alkyl radical.

4. A method according to claim 1, wherein Z is chosen from:

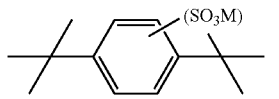

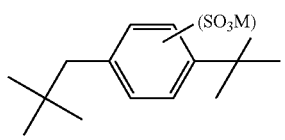

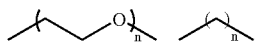

wherein n is defined as in claim 1.

5. A method according to claim 1, wherein the at least one disulphide dye is chosen such that v is equal to 0.

6. A method according to claim 1, wherein in formulae (I), (II), (III) or (IV), A and A' are chosen from radicals comprising at least one chromophore derived from dyes chosen from: acridines, acridones, anthranthrones, anthrapyrimidines, anthraquinones, azines, azos, azomethines, benzanthrones, benzimidazoles, benzimidazolones, benzindoles, benzoxazoles, benzopyrans, benzothiazoles, benzoquinones, bisazines, bisisoindolines, carboxanilides, coumarins, cyanins, diazines, diketopyrrolopyrroles, dioxazines, diphenylamines, diphenylmethanes, dithiazines, flavonoids, fluorindines, formazans, hydrazones, hydroxy ketones, indamines, indanthrones, indigoids and pseudo-indigoids, indophenols, indoanilines, isoindolines, isoindolinones, isoviolanthrones, lactones, methines, naphthalimides, naphthanilides, naphtholactams, naphthoquinones, nitro dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, and xanthenes.

7. A method according to claim 6, wherein in formulae (I), (II), (III) or (IV), A and A' are chosen from radicals comprising a chromophore chosen from azo, anthraquinone and hydrazone chromophores.

8. A method according to claim 1, wherein the at least one disulphide dye is chosen from the following compounds:

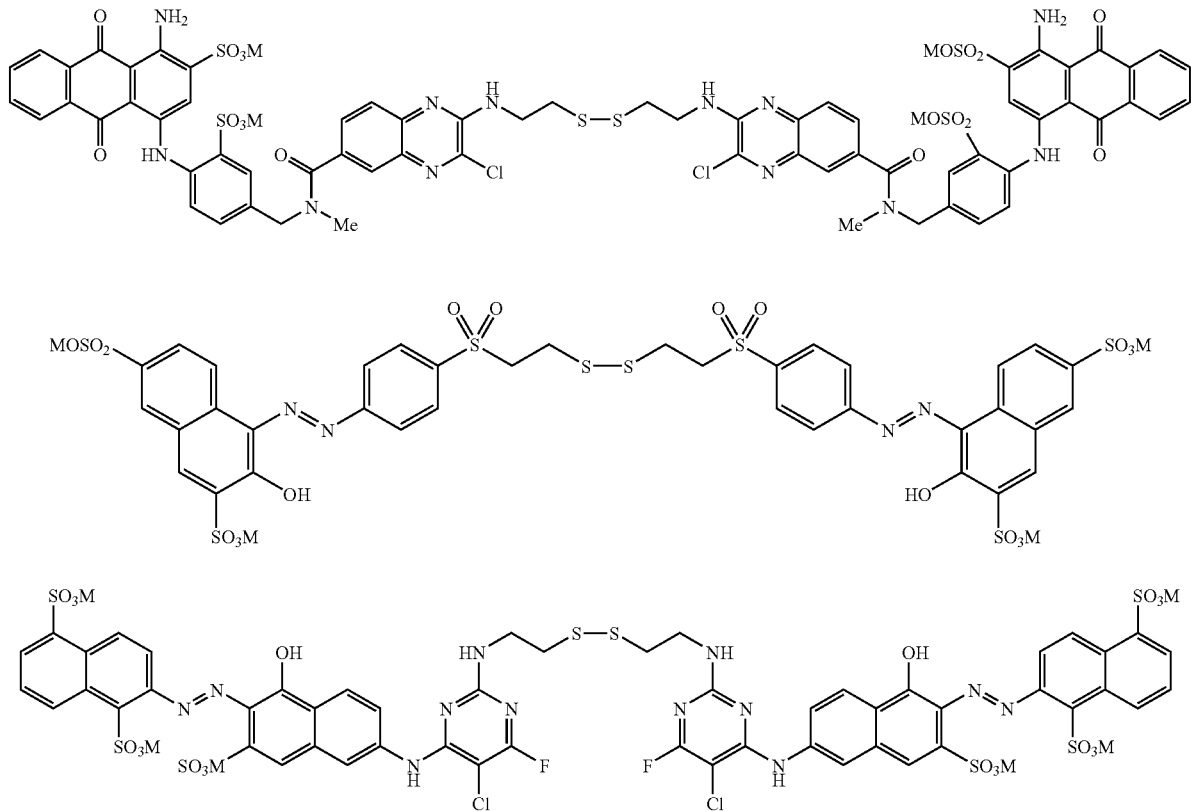

wherein M is chosen from a hydrogen atom, an alkali metal, an ammonium group and an ammonium group substituted with at least one identical or different, linear or branched $C_1$-$C_{10}$ alkyl radical optionally bearing at least one hydroxyl, and from the following compounds, in acidic, basic or neutralized form:

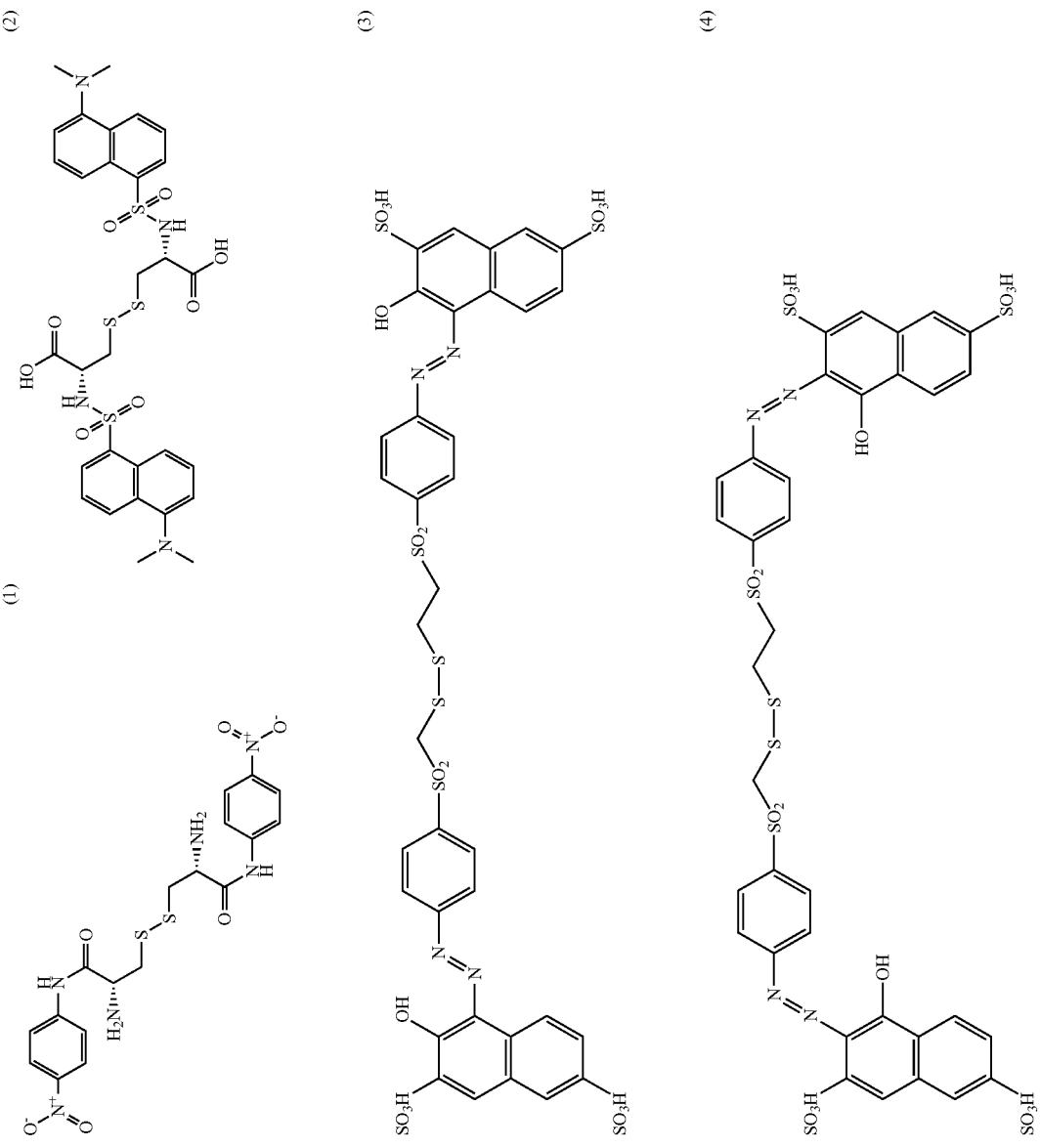

-continued
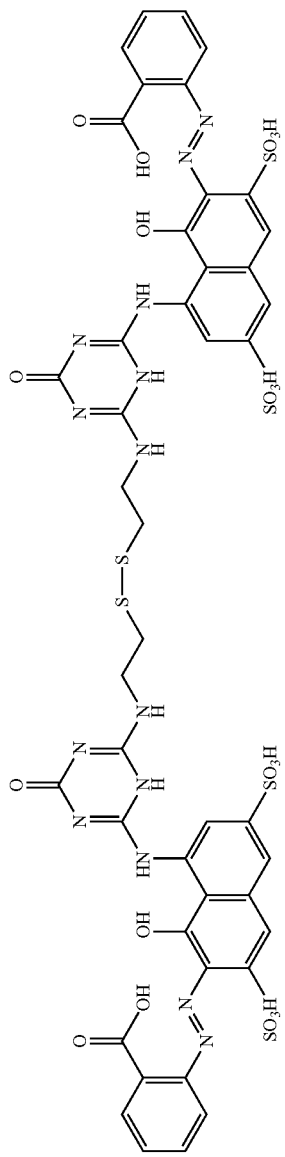
(5)
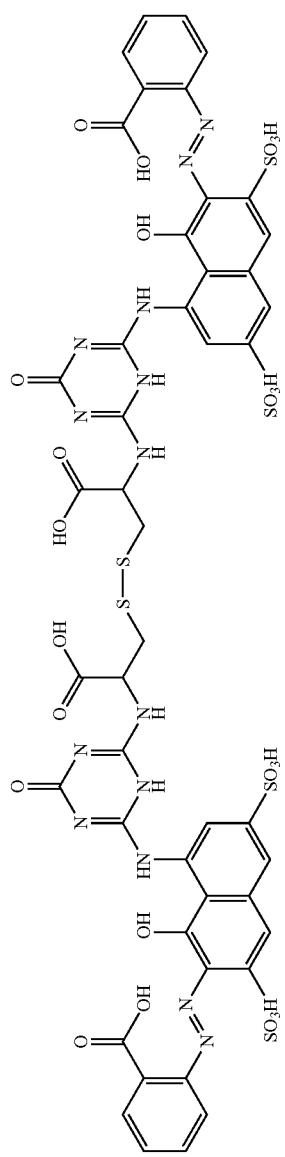
(6)
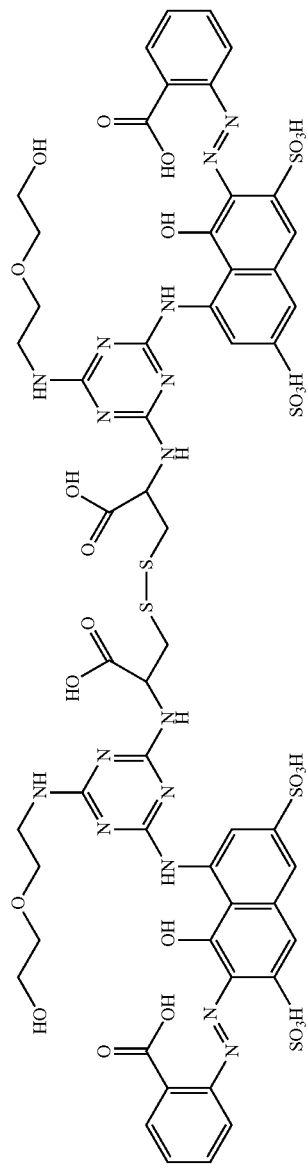
(7)

-continued
(8)
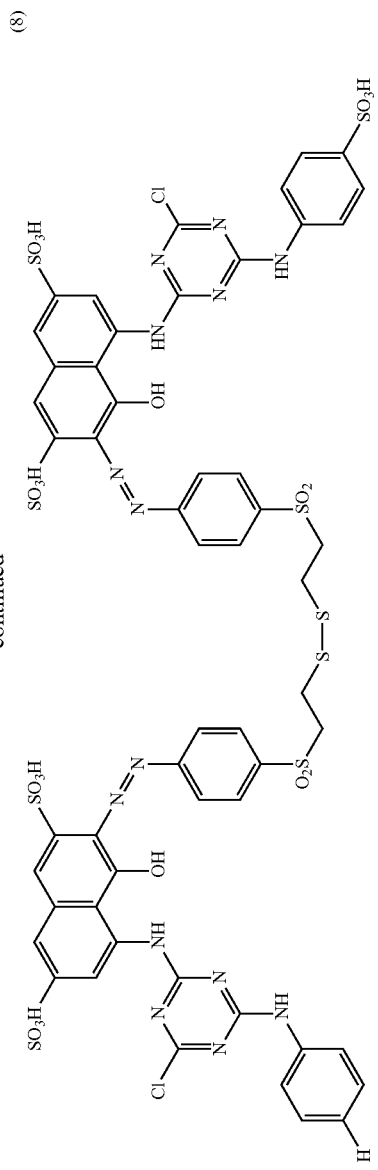
(9)
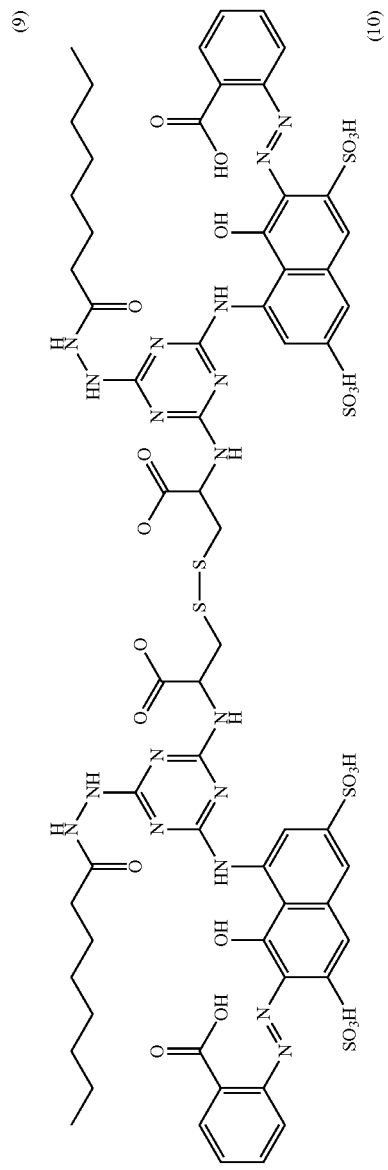
(10)
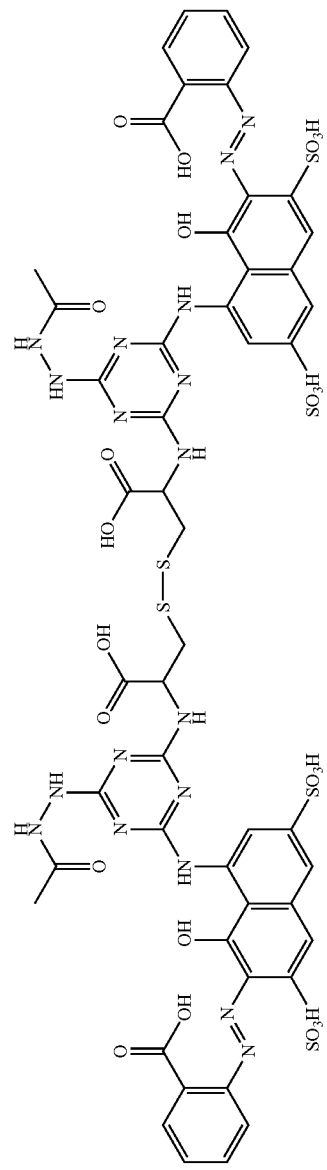

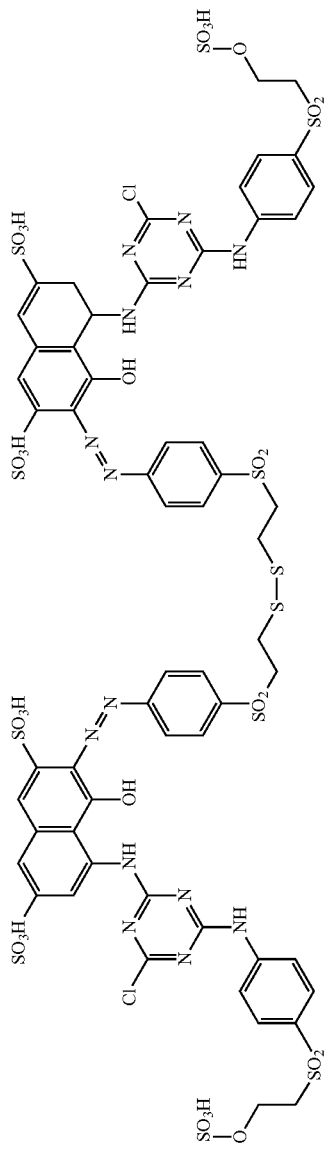
(11)
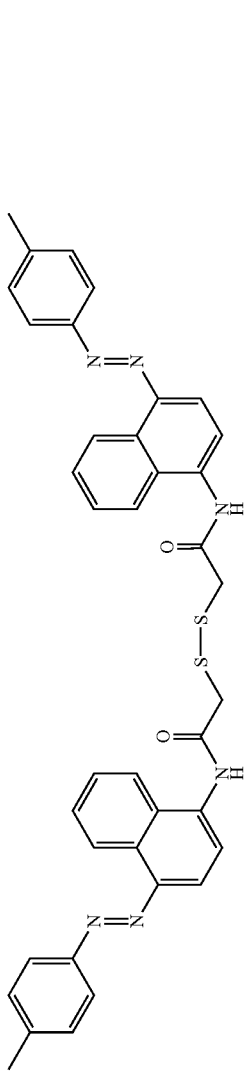
(12)
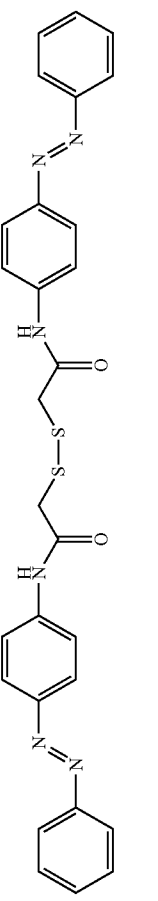
(13)
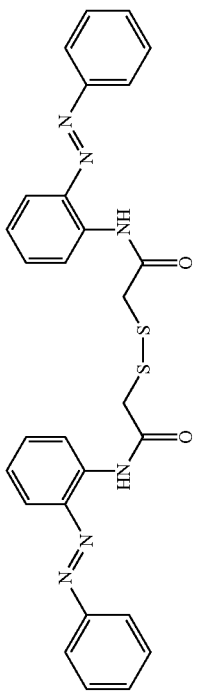
(14)

-continued
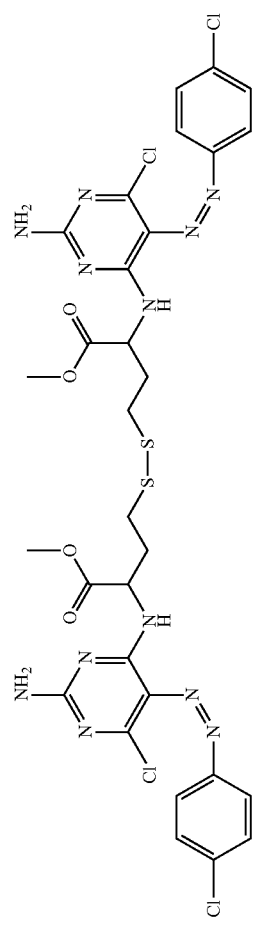
(15)
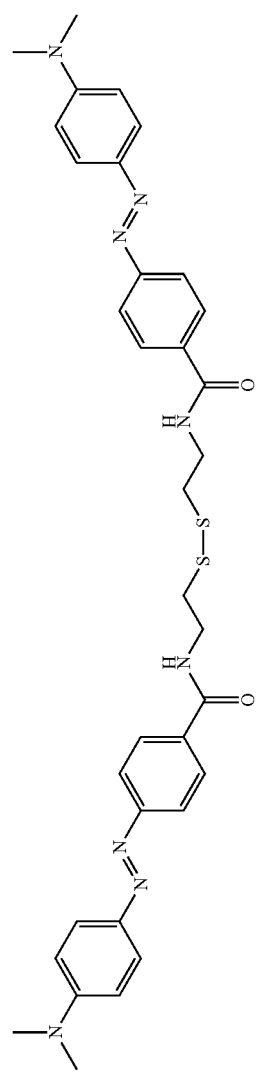
(16)
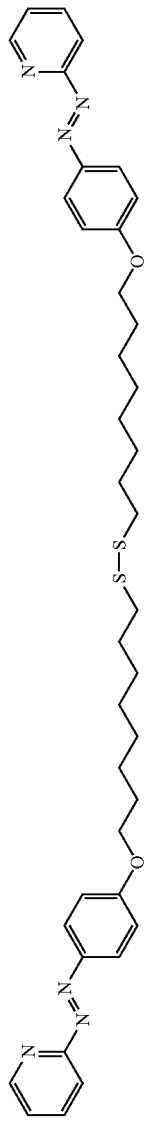
(17)
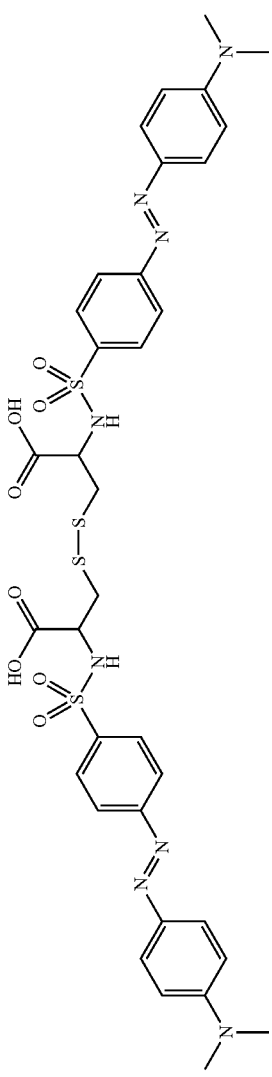
(18)

(21)
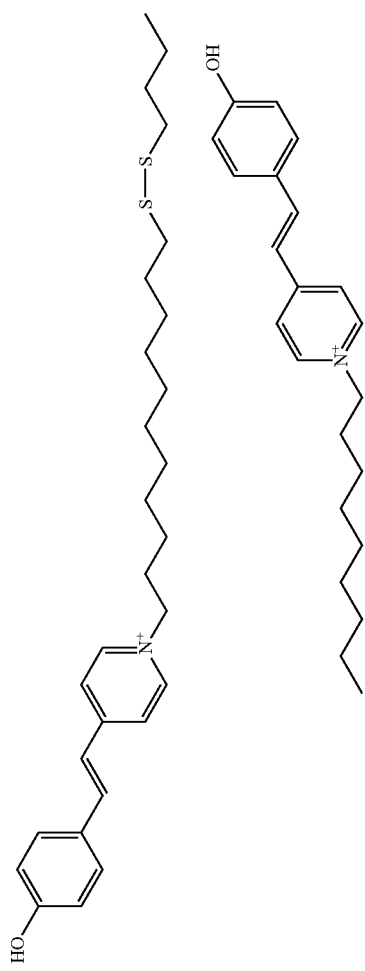
(22)
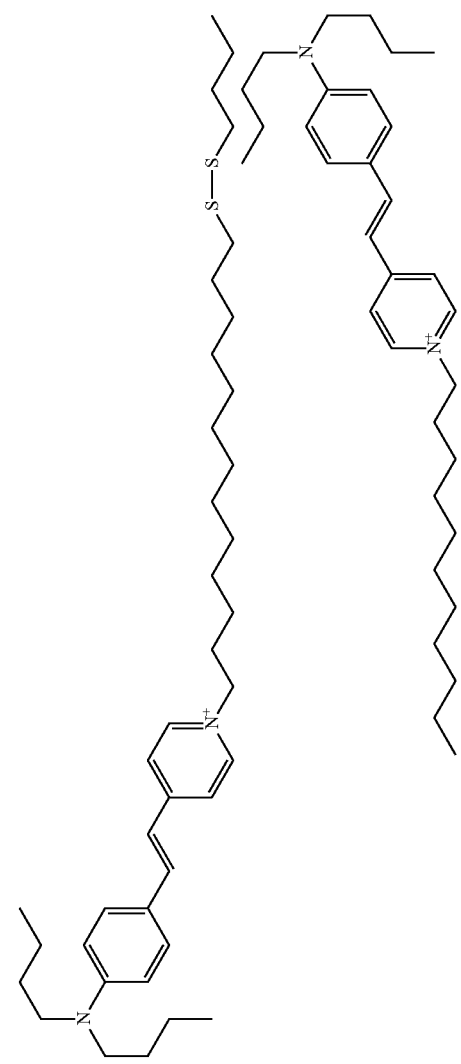
(23)
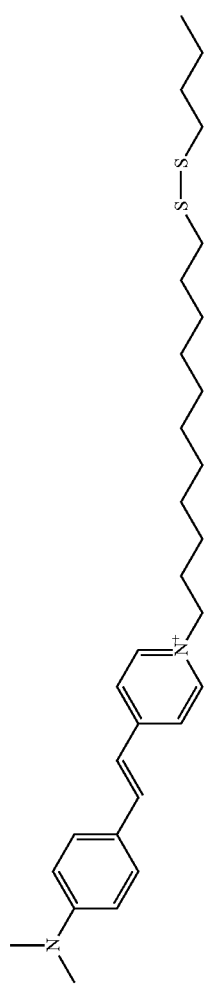

-continued
(24)
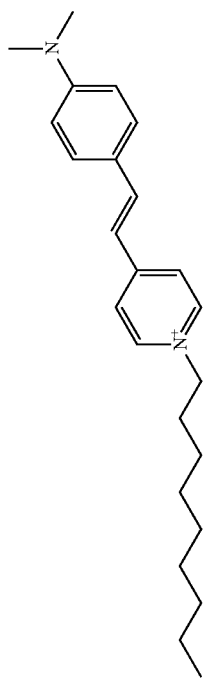
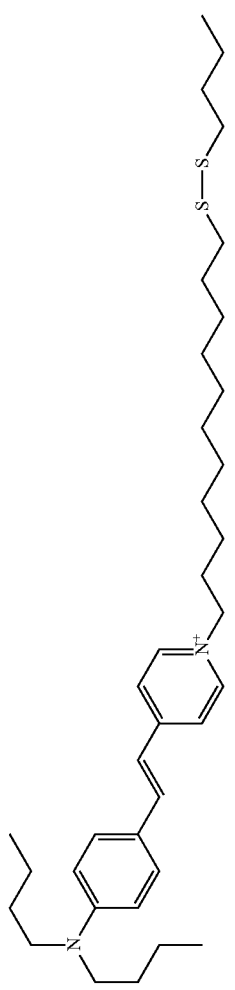
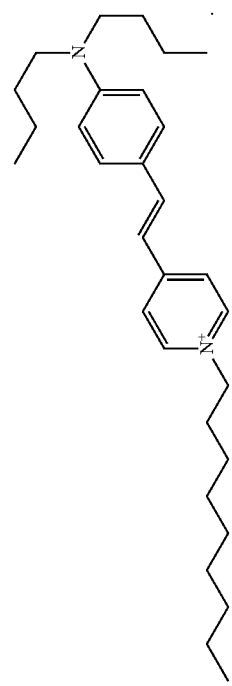

9. A method according to claim 7, wherein in formulae (I), (II), (III) or (IV), A and A' independently comprise at least one cationic chromophore.

10. A method according to claim 9, wherein the at least one cationic chromophore comprises a cationic radical which is a quaternary ammonium.

11. A method according to claim 9, wherein the at least one disulphide dye is chosen such that A is chosen from W—N=N—Ar— and —W—N=N—Ar, wherein W is a fused or nonfused, aromatic or nonaromatic heterocycle comprising a quaternary ammonium; Ar is chosen from a $C_5$ or $C_6$ aryl radical and an aromatic bicycle of the naphthyl type, which are optionally substituted with at least one halogen atom; with at least one alkyl group; with at least one hydroxyl group; with at least one alkoxy group, with at least one hydroxyalkyl group, with at least one amino group or (di) alkylamino group.

12. A method according to claim 11, wherein the at least one disulphide dye is chosen such that p is equal to 1, y and z are equal to zero and T is —N(R)— at the para-position on Ar with respect to the azo functional group.

13. A method according to claim 11, wherein W is chosen from imidazolium, pyridinium, benzimidazolium, pyrazolium, and benzothiazolium groups which are optionally substituted with at least one identical or different $C_1$-$C_4$ alkyl radical.

14. A method according to claim 1, wherein the at least one disulphide dye is chosen from:

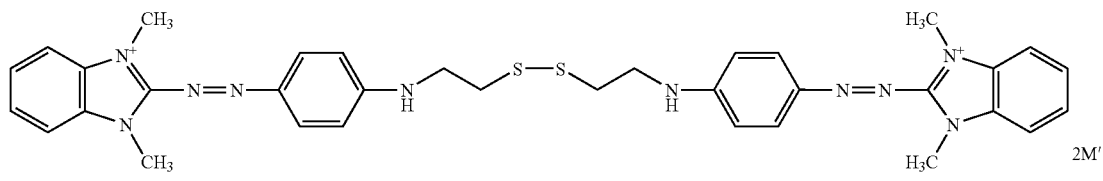

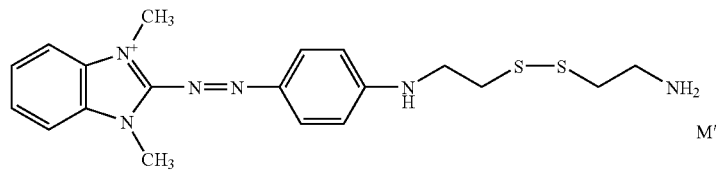

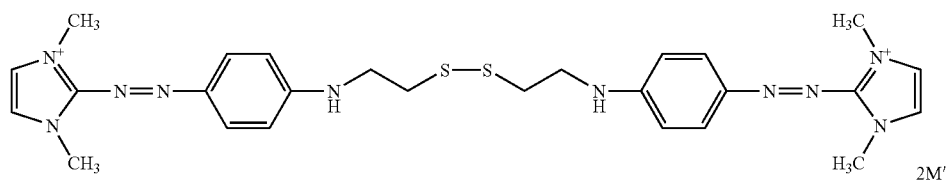

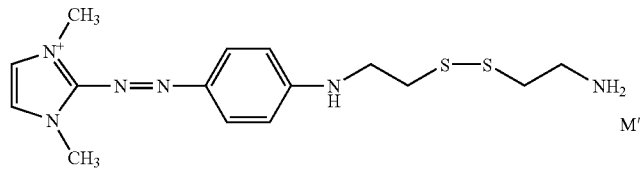

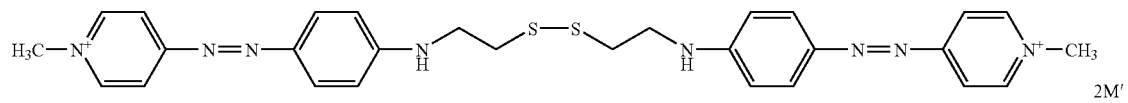

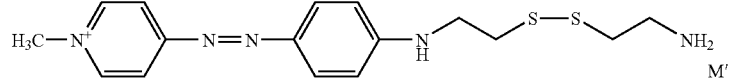

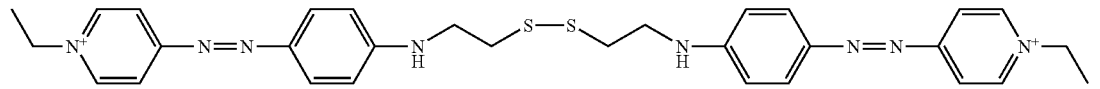

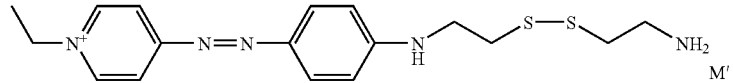

-continued

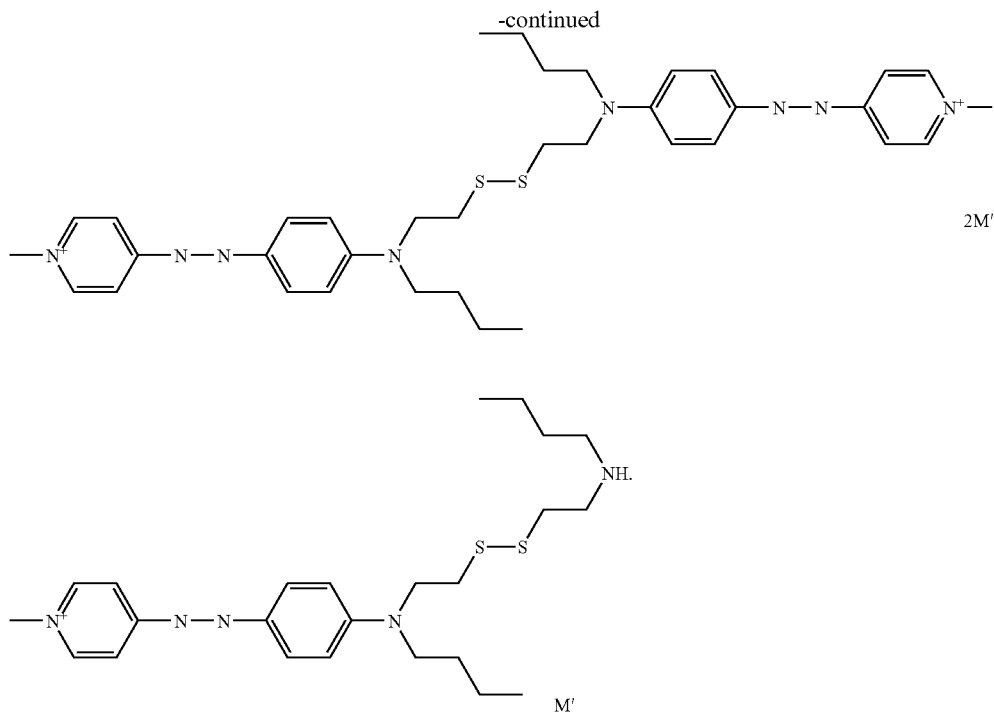

15. A method according to claim 1, wherein the dyeing composition further comprises at least one reducing agent.

16. A method according to claim 1, comprising pre-treating the keratin fibers with at least one reducing agent before applying the dyeing composition.

17. A method according to claim 1, comprising treating the keratin fibers with at least one reducing agent after applying the dyeing composition (post-treatment).

18. A method according to claim 15, wherein the at least one reducing agent is chosen from thiols, phosphines, bisulphite and sulphites.

19. A method according to claim 18, wherein the at least one reducing agent is chosen from thioglycolic acid, cysteine, homocysteine, thiolactic acid and the salts of these thiols.

20. A method according to claim 15, wherein the at least one reducing agent is chosen from borohydrides or derivatives thereof.

21. A method according to claim 20, wherein said borohydrides or derivatives thereof are chosen from borohydride, cyanoborohydride, triacetoxyborohydride and trimethoxyborohydride salts of sodium, lithium, potassium, calcium and quaternary ammonium; and catecholborane.

22. A method according to claim 16, wherein the at least one reducing agent is chosen from thiols, phosphines, bisulphite and sulphites.

23. A method according to claim 22, wherein the at least one reducing agent is chosen from thioglycolic acid, cysteine, homocysteine, thiolactic acid and the salts of these thiols.

24. A method according to claim 16, wherein the at least one reducing agent is chosen from borohydrides or derivatives thereof.

25. A method according to claim 24, wherein said borohydrides or derivatives thereof are chosen from borohydride, cyanoborohydride, triacetoxyborohydride and trimethoxyborohydride salts of sodium, lithium, potassium, calcium and quaternary ammonium; and catecholborane.

26. A method according to claim 17, wherein the at least one reducing agent is chosen from thiols, phosphines, bisulphite and sulphites.

27. A method according to claim 26, wherein the at least one reducing agent is chosen from thioglycolic acid, cysteine, homocysteine, thiolactic acid and the salts of these thiols.

28. A method according to claim 17, wherein the at least one reducing agent is chosen from borohydrides or derivatives thereof.

29. A method according to claim 28, wherein said borohydrides or derivatives thereof are chosen from borohydride, cyanoborohydride, triacetoxyborohydride and trimethoxyborohydride salts of sodium, lithium, potassium, calcium and quaternary ammonium; and catecholborane.

30. A method according to claim 1, wherein the dyeing composition further comprises at least one oxidizing agent.

31. A method according to claim 1, comprising post-treating the keratin fibers with at least one oxidizing agent.

32. A method according to claim 1, comprising post-treating the keratin fibers with at least one conditioning agent and optionally also post-treating the keratin fibers with at least one oxidizing agent.

33. A method according to claim 30, in which the oxidizing agent is chosen from hydrogen peroxide, urea peroxide, alkali metal bromates, persalts, and enzymes.

34. A method according to claim 31, in which the oxidizing agent is chosen from hydrogen peroxide, urea peroxide, alkali metal bromates, persalts, and enzymes.

35. A method according to claim 1, wherein the at least one disulphide dye is present in the dyeing composition in an amount ranging from 0.001 to 50% by weight, relative to the total weight of the composition.

36. A method according to claim 35, wherein the at least one disulphide dye is present in the dyeing composition in an amount ranging from 0.01 to 5% by weight relative to the total weight of the composition.

37. A method according to claim 1, wherein said dyeing composition further comprises at least one additional disulphide compound different from the compound of formula (I), (II), (III) or (IV).

38. A method according to claim 37, wherein the at least one additional disulphide compound other than the compounds of formula (I), (II), (III) or (IV) is chosen from compounds comprising at least one fatty chain.

39. A method according to claim 1, wherein the dyeing composition further comprises at least one additional dyeing ingredient chosen from at least one oxidation base, at least one coupler and at least one direct dye other than a disulphide dye.

40. A dyeing composition comprising, in an appropriate cosmetic medium, at least one disulphide dye chosen from the dyes of the following formulae (I), (II), (III) or (IV):

$$A—(X)_p—C_{sat}—S—S—C_{sat}—(X)_p—A \quad (I)$$

$$A'—(X)_p—C_{sat}—S—S—C_{sat}—(X)_p—A' \quad (II)$$
$$\underset{(V)_v}{\underline{\phantom{XXXXXXXXXXXXXX}}}$$

$$A—(X)_p—C'_{sat}—S—S—C_{sat} \quad (III)$$
$$\underset{(V')_{v'}}{\underline{\phantom{XXXXXX}}}$$

$$A—(X)_p—C_{sat}—S—S—C_{sat}—(X)_p—D \quad (IV)$$

their salts, isomers and solvates,
in which formulae:
  A and A', which are identical or different, are chosen from radicals compositing at least one cationic or noncationic chromophore;
  V and V', which are identical or different, are chosen from bridging groups;
  v and v', which are identical or different, are 0 or 1;
  X, which are identical or different, are chosen from saturated or unsaturated, linear or branched $C_1$-$C_{30}$ hydrocarbon chains optionally interrupted and/or optionally terminated at one or both ends by at least one divalent group, chosen from:
    —N(R)—, —N$^+$(R)(R)—, —O—, —S—, —CO—, —SO$_2$— with R, which are identical or different, being chosen from hydrogen, a $C_1$-$C_4$ alkyl radical, a hydroxyalkyl radical and a aminoalkyl radical;
    an optionally substituted, saturated or unsaturated, fused or nonfused, aromatic or nonaromatic (hetero)cyclic radical optionally comprising at least one identical or different heteroatom;
  the coefficient p is equal to 0 or 1;
  $C_{sat}$, $C'_{sat}$, which are identical or different, are chosen from optionally substituted, optionally cyclic, linear or branched $C_1$-$C_{18}$ alkylene chains;
  D is a radical chosen from hydroxyl, hydroxyalkyl, alkoxy, carboxyl, carboxylate, amino, alkylamino and dialkylamino radicals.

41. A composition according to claim 40, wherein the disulphide dye of formula (I) is different from the following dye:

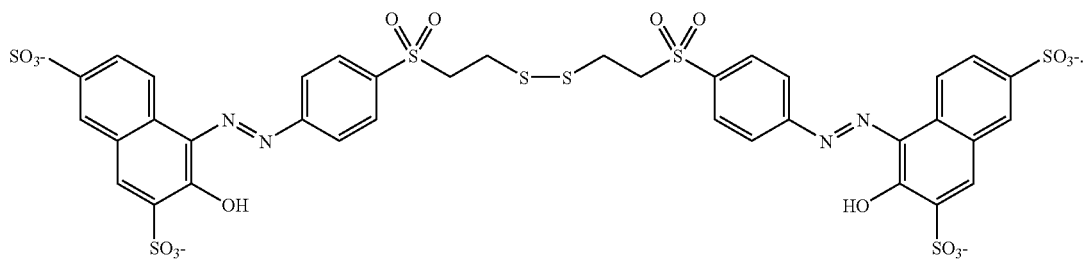

42. A composition according to claim 40, wherein the at least one disulphide dye is chosen such that A is chosen from W—N=N—Ar— and —W—N=N—Ar, wherein W is a fused or nonfused, aromatic or nonaromatic heterocycle comprising a quaternary ammonium; Ar is chosen from $C_5$ or $C_6$ aryl radicals and aromatic bicycles of the naphthyl type, which are optionally substituted with at least one halogen atom; with at least one alkyl group; with at least one hydroxyl group; with at least one alkoxy group, with at least one hydroxyalkyl group, with at least one amino group or (di) alkylamino group.

43. A composition according to claim 42, wherein the at least one disulphide dye is chosen such that p is equal to 1, y and z are equal to zero and T is —N(R)—.

44. A composition according to claim 42, wherein W is chosen from imidazolium, pyridinium, benzimidazolium, pyrazolium, and benzothiazolium which are optionally substituted with at least one identical or different $C_1$-$C_4$ alkyl radical.

45. A composition according to claim 40, further comprising at least one additional dyeing ingredient chosen from at least one oxidation base, at least one coupler and at least one direct dye other than a disulphide dye.

46. A composition according to claim 40, further comprising at least one oxidizing agent.

47. A composition according to claim 40, further comprising at least one organic solvent and/or at least one thickening agent.

48. A multicompartment device in which a first compartment comprises a dyeing composition, and a second compartment comprises at least one reducing agent capable of reducing a disulphide bond,
  wherein said dyeing composition comprises, in an appropriate cosmetic medium, at least one disulphide dye chosen from the dyes of the following formulae (I), (II), (III) or (IV):

$$A—(X)_p—C_{sat}—S—S—C_{sat}—(X)_p—A \quad (I)$$

-continued $$A'-(X)_p-C_{sat}-S-S-C_{sat}-(X)_p-A' \quad (II)$$
$$\lfloor\text{———}(V)_v\text{———}\rfloor$$

$$A-(X)_p-C'_{sat}-S-S-C_{sat} \quad (III)$$
$$\lfloor\text{——}(V')_{v'}\text{——}\rfloor$$

$$A-(X)_p-C_{sat}-S-S-C_{sat}-(X)_p-D \quad (IV)$$

their salts, isomers and solvates,
in which formulae:

A and A', which are identical or different, are chosen from radicals compositing at least one cationic or noncationic chromophore;

V and V', which are identical or different, are chosen from bridging groups;

v and v', which are identical or different, are 0 or 1;

X, which are identical or different, are chosen from saturated or unsaturated, linear or branched $C_1$-$C_{30}$ hydrocarbon chains optionally interrupted and/or optionally terminated at one or both ends by at least one divalent group, chosen from:
—N(R)—, —N$^+$(R)(R)—, —O—, —S—, —CO—, —SO$_2$— with R, which are identical or different, being chosen from hydrogen, a $C_1$-$C_4$ alkyl radical, a hydroxyalkyl radical and a aminoalkyl radical;
an optionally substituted, saturated or unsaturated, fused or nonfused, aromatic or nonaromatic (hetero)cyclic radical optionally comprising at least one identical or different heteroatom;

the coefficient p is equal to 0 or 1;

$C_{sat}$, $C'_{sat}$, which are identical or different, are chosen from optionally substituted, optionally cyclic, linear or branched $C_1$-$C_{18}$ alkylene chains;

D is a radical chosen from hydroxyl, hydroxyalkyl, alkoxy, carboxyl, carboxylate, amino, alkylamino and dialkylamino radicals.

49. A multicompartment device according to claim 48, further comprising a third compartment which comprises at least one oxidizing agent.

50. A method according to claim 1, wherein said keratin fibers are human hair.

51. A method for improving the fastness of coloration on keratin fibers, said method comprising applying to keratin fibers a dyeing composition comprising, in an appropriate cosmetic medium, at least one disulphide dye chosen from the dyes of the following formulae (I), (II), (III) or (IV):

$$A-(X)_p-C_{sat}-S-S-C_{sat}-(X)_p-A \quad (I)$$

$$A'-(X)_p-C_{sat}-S-S-C_{sat}-(X)_p-A' \quad (II)$$
$$\lfloor\text{———}(V)_v\text{———}\rfloor$$

$$A-(X)_p-C'_{sat}-S-S-C_{sat} \quad (III)$$
$$\lfloor\text{——}(V')_{v'}\text{——}\rfloor$$

$$A-(X)_p-C_{sat}-S-S-C_{sat}-(X)_p-D \quad (IV)$$

their salts, isomers and solvates,
in which formulae:

A and A', which are identical or different, are chosen from radicals compositing at least one cationic or noncationic chromophore;

V and V', which are identical or different, are chosen from bridging groups;

v and v', which are identical or different, are 0 or 1;

X, which are identical or different, are chosen from saturated or unsaturated, linear or branched $C_1$-$C_{30}$ hydrocarbon chains optionally interrupted and/or optionally terminated at one or both ends by at least one divalent group, chosen from:
N(R)—, —N$^+$(R)(R)—, —O—, —S—, —CO—, —SO$_2$— with R, which are identical or different, being chosen from hydrogen, a $C_1$-$C_4$ alkyl radical, a hydroxyalkyl radical and a aminoalkyl radical;
an optionally substituted, saturated or unsaturated, fused or nonfused, aromatic or nonaromatic (hetero)cyclic radical optionally comprising at least one identical or different heteroatom;

the coefficient p is equal to 0 or 1;

$C_{sat}$, $C'_{sat}$, which are identical or different, are chosen from optionally substituted, optionally cyclic, linear or branched $C_1$-$C_{18}$ alkylene chains;

D is a radical chosen from hydroxyl, hydroxyalkyl, alkoxy, carboxyl, carboxylate, amino, alkylamino and dialkylamino radicals.

52. A cationic disulphide dye comprising at least one quaternary ammonium radical of the following formulae (I), (II), (III) or (IV):

$$A-(X)_p-C_{sat}-S-S-C_{sat}-(X)_p-A \quad (I)$$

$$A'-(X)_p-C_{sat}-S-S-C_{sat}-(X)_p-A' \quad (II)$$
$$\lfloor\text{———}(V)_v\text{———}\rfloor$$

$$A-(X)_p-C'_{sat}-S-S-C_{sat} \quad (III)$$
$$\lfloor\text{——}(V')_{v'}\text{——}\rfloor$$

$$A-(X)_p-C_{sat}-S-S-C_{sat}-(X)_p-D \quad (IV)$$

their salts, isomers and solvates,
in which formulae:

A and A', which are identical or different, are chosen from radicals comprising at least one cationic chromophore belonging to the azo, anthraquinone or hydrazone families;

V and V', which are identical or different, are chosen from bridging groups;

v and v', which are identical or different, are 0 or 1;

X represents the following sequence:

$$-(T)_t-(Y)_y-(Z)_z-$$

the said sequence being linked in formulae (I), (II), (III) or (IV) as follows:

—$C_{sat}$(or $C'_{sat}$)-(T)$_t$-(Y)$_y$-(Z)$_z$-(A or A'); in which

T is chosen from at least one radical chosen from —SO$_2$—, —O—, —S—, —N(R)—, —N+(R)(R)—CO—, wherein R is chosen from a hydrogen atom, a $C_1$-$C_4$ alkyl radical and a $C_1$-$C_4$ hydroxyalkyl radical;

the coefficient t is equal to 0 or 1;

Y is chosen from:

a radical chosen from —(CH$_2$)$_2$—SO$_2$—; —CH$_2$—CHR—CO—NR'— wherein R and R', which are identical or different, are chosen from a hydrogen atom and a C$_1$-C$_4$ alkyl radical;

a group of formula (a), (a') or (a"):

(a)

(a')

(a")

in which

B is chosen from —N—, —CR$_a$, wherein R$_a$ is chosen from a hydrogen atom, a halogen atom chosen from chlorine or fluorine, a nitro group, a pyridinium group which is optionally substituted;

R' has the same definition as above

R'$_a$ is chosen from:
- a hydrogen atom
- a chlorine atom or a fluorine atom
- a pyridinium group which is optionally substituted with at least one group R$_c$, it being possible for R$_c$ to be a C$_1$-C$_4$ alkyl group, a halogen atom, a carboxyl group —COOM (wherein M is chosen from a hydrogen atom, an alkali metal, an ammonium group and an ammonium group substituted with at least one linear or branched, identical or different C$_1$-C$_{18}$ alkyl radical, optionally bearing at least one hydroxyl); an ester group —COOR$_d$ wherein R$_d$ is a C$_1$-C$_4$ alkyl radical; an amide group —CON(R$_d$)$_2$ wherein R$_d$, which are identical or different, are chosen from a hydrogen atom and a C$_1$-C$_4$ alkyl radical;
- a hydroxyl group
- an amino, alkylamino or dialkylamino group, the alkyl group of which being chosen from identical or different C$_1$-C$_{18}$ alkyl groups which are linear or branched, optionally interrupted by a heteroatom chosen from N and O, and which are optionally substituted with at least one hydroxyl group,
- a group NHNHCOR where R is a linear or branched C$_1$-C$_{10}$ alkyl group a group of the following formula (b):

in which

R' has the same definition as above

R$_b$ is chosen from
- a chlorine atom
- an amino, alkylamino or dialkylamino group, the alkyl group thereof being chosen from identical or different C$_1$-C$_{18}$ alkyl groups which are linear or branched, optionally interrupted by a heteroatom chosen from N, O, and S, and which are optionally substituted with at least one hydroxyl group,
- a saturated or unsaturated nitrogen-containing heterocycle which may be substituted
- an arylamino group;

the coefficient p is equal to 1;

y is equal to 0 or 1;

Z is chosen from:
- —(CH$_2$)$_m$— wherein m is an integer from 1 to 8
- —(CH$_2$CH$_2$O)$_q$— or —(OCH$_2$CH$_2$)$_q$— in which q is an integer from 1 to 15
- an aryl, alkylaryl or arylalkyl radical whose alkyl radical is C$_1$-C$_4$, being optionally substituted with at least one group SO$_3$M wherein M is chosen from a hydrogen atom, an alkali metal, an ammonium group and an ammonium group substituted with at least one identical or different, linear or branched C$_1$-C$_{18}$ alkyl radical optionally bearing at least one hydroxyl group, z is equal to 0 or 1;

C$_{sat}$, C'$_{sat}$, which are identical or different, are chosen from optionally substituted, optionally cyclic, linear or branched C$_1$-C$_{18}$ alkylene chains;

D is to a radical chosen from hydroxyl, hydroxyalkyl, alkoxy, carboxyl, carboxylate, amino, alkylamino and dialkylamino radicals.

53. A dye according to claim 52, wherein A or A', which are identical or different, comprise an azo chromophore.

54. A dye according to claim 52, wherein the disulphide dye is chosen such that y and z are equal to zero and T is —N(R)—.

55. A dye according to claim 52, wherein W is chosen from imidazolium, pyridinium, benzimidazolium, pyrazolium, and benzothiazolium which are optionally substituted with at least one identical or different C$_1$-C$_4$ alkyl radical.

56. A dye according to claim 52, wherein the disulphide dye is chosen from:
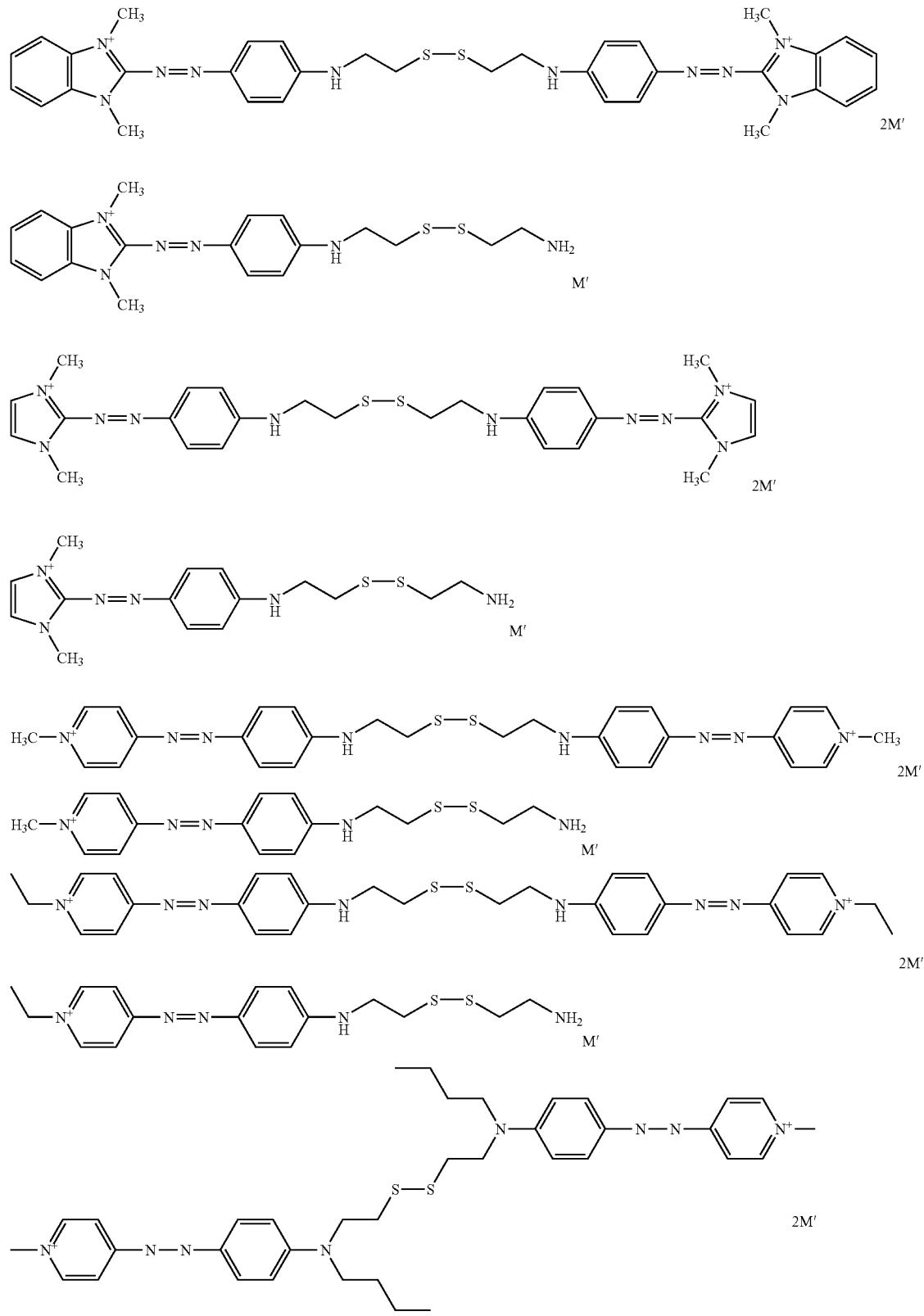

-continued
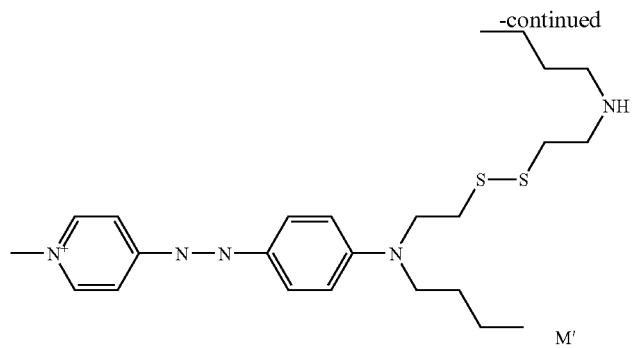
M'
57. A dye of the following formulae:
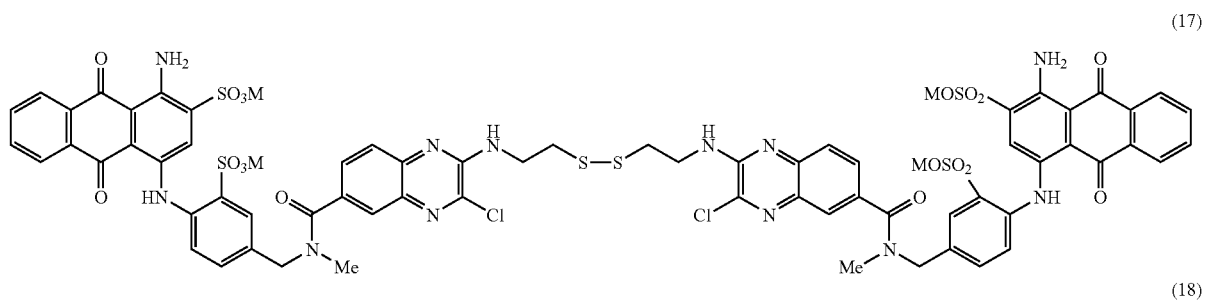
(17)
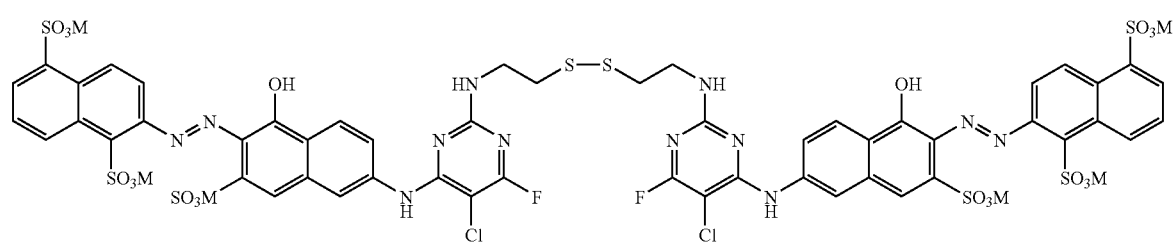
(18)
wherein M is chosen from a hydrogen atom, an alkali metal, an ammonium group and an ammonium group substituted with at least one identical or different, linear or branched $C_1$-$C_{10}$ alkyl radical optionally bearing at least one hydroxyl, wherein the dye is in acidic, basic or neutralized form.
* * * * *

UNITED STATES PATENT AND TRADEMARK OFFICE
CERTIFICATE OF CORRECTION

PATENT NO. : 7,488,354 B2
APPLICATION NO. : 11/249357
DATED : February 10, 2009
INVENTOR(S) : Nicolas Daubresse et al.

It is certified that error appears in the above-identified patent and that said Letters Patent is hereby corrected as shown below:

In claim 8, col. 51, compound 8,

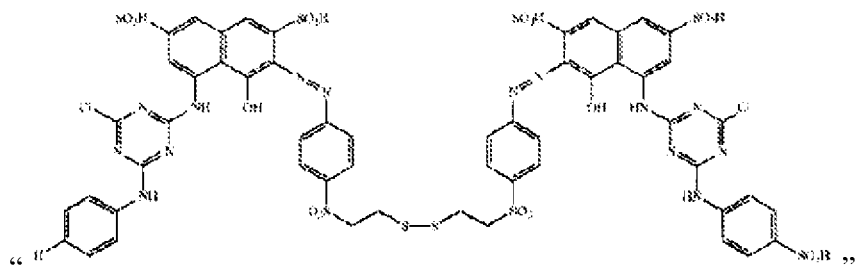

should read:

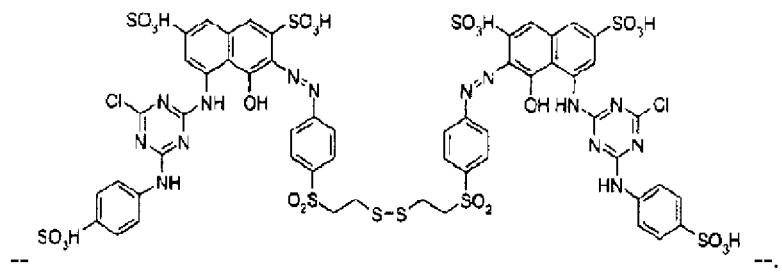

In claim 8, col. 57, compound 21,

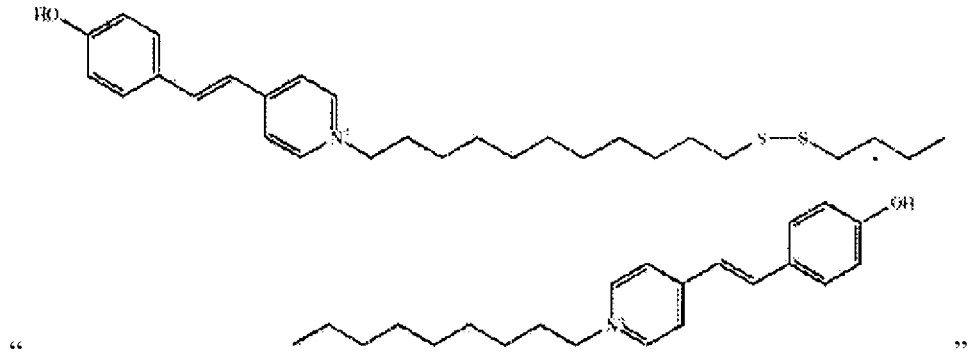

UNITED STATES PATENT AND TRADEMARK OFFICE
CERTIFICATE OF CORRECTION

PATENT NO.         : 7,488,354 B2
APPLICATION NO. : 11/249357
DATED                  : February 10, 2009
INVENTOR(S)         : Nicolas Daubresse et al.

It is certified that error appears in the above-identified patent and that said Letters Patent is hereby corrected as shown below:

should read:

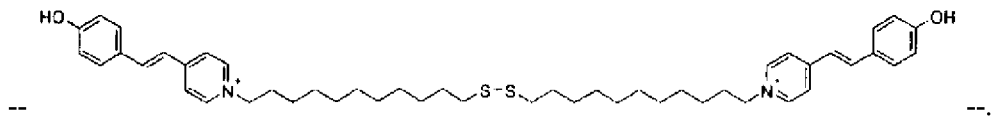

In claim 8, col. 58, compound 22,

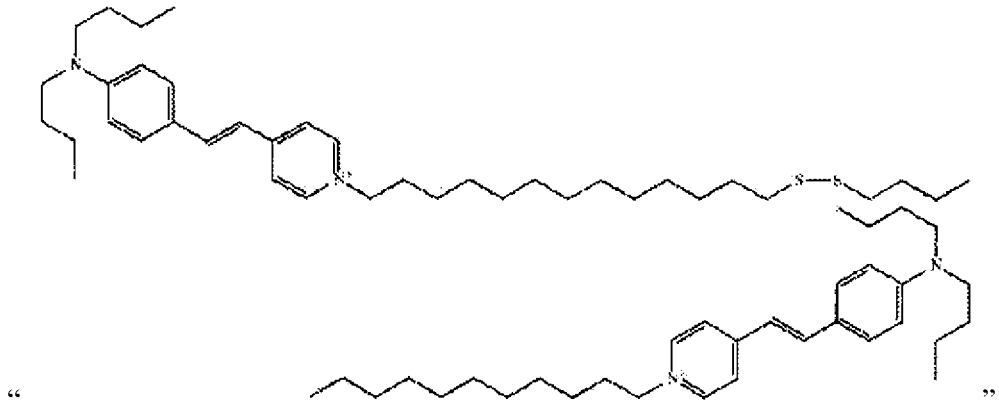

should read:

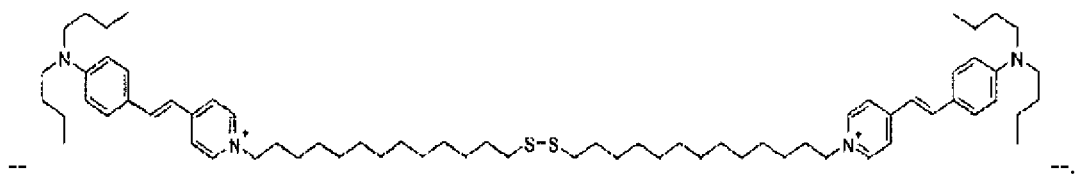

UNITED STATES PATENT AND TRADEMARK OFFICE
CERTIFICATE OF CORRECTION

PATENT NO.       : 7,488,354 B2
APPLICATION NO.  : 11/249357
DATED            : February 10, 2009
INVENTOR(S)      : Nicolas Daubresse et al.

It is certified that error appears in the above-identified patent and that said Letters Patent is hereby corrected as shown below:

In claim 8, col. 59 and col. 60, compound 23,

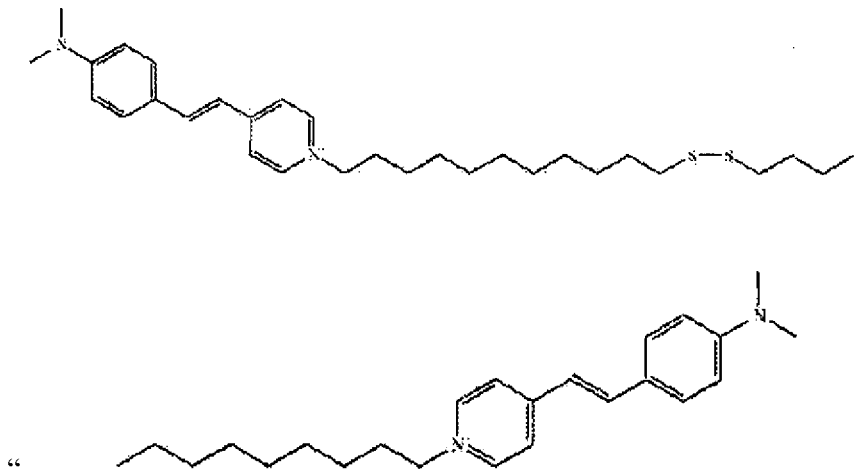

should read:

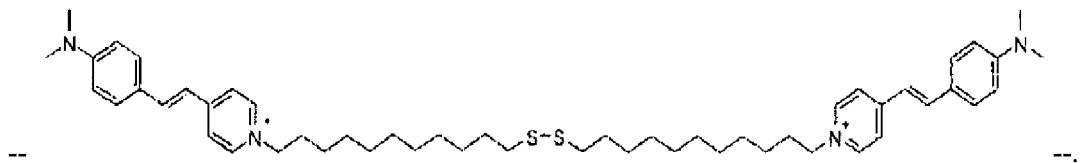

UNITED STATES PATENT AND TRADEMARK OFFICE
CERTIFICATE OF CORRECTION

PATENT NO. : 7,488,354 B2
APPLICATION NO. : 11/249357
DATED : February 10, 2009
INVENTOR(S) : Nicolas Daubresse et al.

It is certified that error appears in the above-identified patent and that said Letters Patent is hereby corrected as shown below:

In claim 8, col. 60, compound 24,

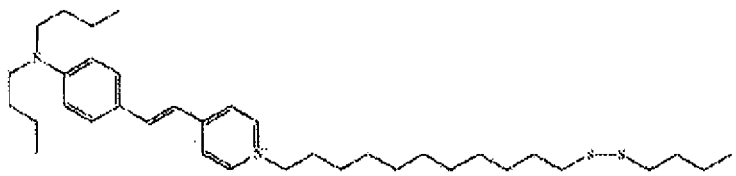

"

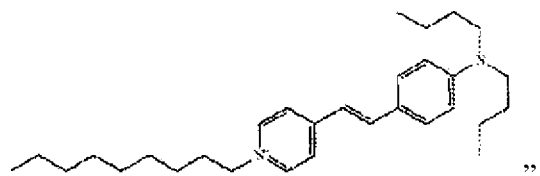

"

should read

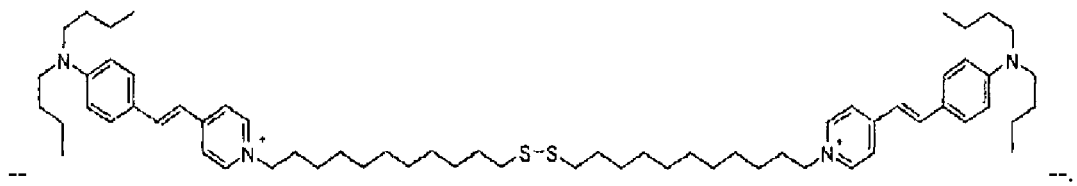

-- -- .

Signed and Sealed this

First Day of December, 2009

David J. Kappos
*Director of the United States Patent and Trademark Office*